(12) United States Patent
Stock et al.

(10) Patent No.: US 8,334,413 B2
(45) Date of Patent: Dec. 18, 2012

(54) TOPICAL COMPOSITIONS AND METHODS FOR EPITHELIAL-RELATED CONDITIONS

(75) Inventors: Jeffry B. Stock, Princeton, NJ (US); Joel Gordon, Princeton Junction, NJ (US); Maxwell Stock, Rocky Hill, NJ (US)

(73) Assignee: Signum Biosciences, Inc., Monmouth Junction, NJ (US)

( * ) Notice: Subject to any disclaimer, the term of this patent is extended or adjusted under 35 U.S.C. 154(b) by 0 days.

(21) Appl. No.: 12/968,800

(22) Filed: Dec. 15, 2010

(65) Prior Publication Data

US 2011/0117187 A1 May 19, 2011

Related U.S. Application Data

(62) Division of application No. 11/151,174, filed on Jun. 13, 2005.

(60) Provisional application No. 60/652,921, filed on Feb. 14, 2005, provisional application No. 60/579,093, filed on Jun. 12, 2004.

(51) Int. Cl.
C07C 381/00 (2006.01)
A61Q 19/00 (2006.01)

(52) U.S. Cl. ............. 568/44; 568/39; 568/45; 424/401; 514/562

(58) Field of Classification Search ........................ None
See application file for complete search history.

(56) References Cited

U.S. PATENT DOCUMENTS

| | | | |
|---|---|---|---|
| 4,294,852 A | 10/1981 | Wildnauer et al. | |
| 4,380,549 A | 4/1983 | Van Scott et al. | |
| 4,552,872 A | 11/1985 | Cooper et al. | |
| 4,612,331 A * | 9/1986 | Barratt et al. | 514/558 |
| 5,019,569 A | 5/1991 | Kligman et al. | |
| 5,043,268 A | 8/1991 | Stock | |
| 5,188,826 A * | 2/1993 | Chandrasekaran et al. | 424/78.04 |
| 5,202,456 A | 4/1993 | Rando | |
| 5,284,867 A | 2/1994 | Kloog et al. | |
| 5,308,840 A | 5/1994 | Sugiyama et al. | |
| 5,455,274 A | 10/1995 | Suh | |
| 5,482,710 A | 1/1996 | Slavtcheff et al. | |
| 5,521,215 A | 5/1996 | Mechoulam et al. | |
| 5,567,729 A * | 10/1996 | Bradfute et al. | 514/546 |
| 5,571,687 A | 11/1996 | Casey et al. | |
| 5,639,768 A | 6/1997 | Morrissey et al. | |
| 5,658,881 A | 8/1997 | Gelland et al. | |
| 5,705,528 A | 1/1998 | Kloog | |
| 5,789,541 A | 8/1998 | Rando | |
| 5,837,224 A | 11/1998 | Voorhees et al. | |
| 6,015,877 A | 1/2000 | Rando | |
| 6,096,740 A | 8/2000 | Mechoulam et al. | |
| 6,114,388 A | 9/2000 | Geffard | |
| 6,159,485 A | 12/2000 | Yu et al. | |
| 6,251,882 B1 | 6/2001 | Uckun et al. | |
| 6,372,793 B1 | 4/2002 | Lamango et al. | |
| 6,403,619 B1 | 6/2002 | Jacobson et al. | |
| 6,414,037 B1 | 7/2002 | Pezzuto et al. | |
| 6,440,966 B1 | 8/2002 | Barrett et al. | |
| 6,462,086 B1 | 10/2002 | Kloog et al. | |
| 6,482,086 B1 | 11/2002 | Rimoto et al. | |
| 6,492,128 B1 | 12/2002 | Haklai et al. | |
| 6,946,485 B2 | 9/2005 | Kloog et al. | |
| 7,365,080 B2 | 4/2008 | Gregor et al. | |
| 7,576,094 B2 | 8/2009 | Chu et al. | |
| 7,846,915 B2 | 12/2010 | Wong et al. | |
| 2002/0010128 A1 | 1/2002 | Parks et al. | |
| 2002/0182237 A1 | 12/2002 | Bissett et al. | |
| 2003/0059450 A1 * | 3/2003 | Maibach et al. | 424/401 |
| 2003/0143288 A1 * | 7/2003 | Mayne et al. | 424/725 |
| 2003/0180719 A1 | 9/2003 | Herget et al. | |
| 2003/0203942 A1 | 10/2003 | Kloog et al. | |
| 2003/0228688 A1 | 12/2003 | Dobie | |
| 2004/0082015 A1 | 4/2004 | Geffard | |
| 2004/0138446 A1 | 7/2004 | Kharrat et al. | |
| 2004/0152073 A1 | 8/2004 | Herget et al. | |
| 2005/0277694 A1 | 12/2005 | Stock et al. | |
| 2007/0004803 A1 | 1/2007 | Gibbs et al. | |

FOREIGN PATENT DOCUMENTS

| | | |
|---|---|---|
| WO | WO-91/17261 A1 | 11/1991 |
| WO | WO-01/07086 A1 | 2/2001 |
| WO | WO 0230453 A1 * | 4/2002 |
| WO | WO-02/060426 A3 | 8/2002 |
| WO | WO-03/018062 A1 | 3/2003 |
| WO | WO-03078448 A1 | 9/2003 |
| WO | WO-2004/042081 A1 | 5/2004 |
| WO | WO-2004/087064 A2 | 10/2004 |
| WO | WO-2006/102126 A2 | 9/2006 |
| WO | WO-2006125930 A1 | 11/2006 |

OTHER PUBLICATIONS

Leonard; J Med Chem 40(19), p. 2971-2990, 1997.*
Aharonson, et al., "Stringent structural requirements for anti-Ras activity of S-prenyl analogues," *Biochim Biophys Acta*, 1406:40-50, (1998).
Ahmad et al., "Role of isoprenylcysteine carboxyl methyltransferase in tumor necrosis factor-alpha stimulation of expression of vascular cell adhesion molecule-1 in endothelial cells," *Arterioscler. Thromb. Vasc. Biol.*, 22:759-764, (2002).

(Continued)

*Primary Examiner* — Nissa Westerberg
(74) *Attorney, Agent, or Firm* — SorinRand LLP

(57) ABSTRACT

The present invention relates to pharmaceutical, cosmetic and cosmeceutical topical compositions containing polyisoprenyl-protein inhibitor compounds and methods useful in the promotion of healthy epithelium and the treatment of epithelial-related conditions.

42 Claims, 13 Drawing Sheets

OTHER PUBLICATIONS

Anderson et al., "Purification, functional reconstitution, and characterization of the *Saccharomyces cerevisiae* isoprenylcysteine carboxylmethyltransferase Ste14p." *J. Biol. Chem.*, 280:7336-7345, (2005).

Anderson et al., "The isoprenoid substrate specificity of isoprenylcysteine carboxylmethyltransferase: development of novel inhibitors" *J. Biol. Chem.*, 280:29454-29461 (2005).

Baron et al., "Analysis of the kinetic mechanism of recombinant human isoprenylcysteine carboxylmethyltransferase (Icmt)" *BMC Biochem* 5:19, (2004).

Bergo et al, (2000), Targeted inactivation of the isoprenylcysteine carboxyl methyltransferase gene causesmislocalizalion of K-Ras in mammalian cells. J. Biol. Chem., 275:17605-17610.

Bergo et al., "Isoprenylcysteine carboxyl methyltransferase deficiency in mice". *J. Biol. Chem.*, 276:5841-5845, (2001).

Boivin et al. (1997) Essential arginine residues in isoprenylcysteine protein carboxyl methyltransferase. Biochem. Cell Biol., 75:63-69.

Brown et al, "Dermal and Transdermal Drug Delivery Systems: Current and Future Prospects" *Drug Delivery*, 13:175-87, (2006).

Capdevila et al. (1997) Pancreatic exocrine secretion is blocked by inhibitors of methylation. Arch. Biochem. Biophys., 345:1:47-55.

Carlson, R.P., et al., (1985) "Modulation of mouse ear edema by cyclooxygenase and lipoxygenase inhibitors and other pharmacologic agents," Agents Actions, vol. 17, No. 2, pp. 197-204.

Chiu et al., (2004) Carboxyl methylation of Ras regulates membrane targeting and effector engagement. J. Biol. Chem., 279:7346-7352.

Choy et al. (1999) Endomembrane trafficking of Ras: the CAAX motif targets proteins to the ER and Golgi. Cell, 98:69-80.

Choy, E. and Philips, M. (2000). Expression and activity of human prenylcysteine-directed carboxyl methyltransferase. Methods Enzymol., 325:101-114.

Clarke et al, "Ras Antagonist Farnesylthiosalicylic Acid (FTS) Reduces Glomerular Cellular Proliferatio and Macrophase Number in Rat Thy-1 Nephritis," *J Am. Soc. Nephrol.* 14:848-854, (2003).

Crowell et al. (1998) Prenylcysteine alpha-carboxyl meth Itransferase in suss ension-cultured tobacco cells. Plant Ph siol. 118:115-123.

Dai et al., (1998) Mammalian prenylcysteine carboxyl methyltransferase is in the endoplasmic reticulum. J. Biol. Chem., 273:15030-15034.

Desrosiers et al., (2000) Modulation of Rho and cytoskeletal protein attachment to membranes by a prenylcysteine analog. *J.* Biol. Chem., 275:14949-14957.

Desrosiers, R.R. and Beliveau, R. (1998) Regulation by GTPgammaS of protein carboxylmethyltransferase activity in kidney brush border membranes. Arch. Biochem. Biophys., 351:149-158.

Desrosiers, R.R. and Beliveau, R. (1999) Guanosine 5'-(3-O-Thio)triphosphate stimulates protein carboxyl methylation in cell membranes. Arch. Biochem. Biophys., 367:333-340.

Dietrich et al.(2003) Studies on G-protein alpha.betagamma heterotrimer formation reveal a putative S-prenyl-binding site in the alpha subunit. Biochem. J., 376:449-456.

Ding et al., (1994) Famesyl-L-cysteine analogs can inhibit or initiate superoxide release by human neutrophils. J. Biol. Chem., 269:16837-16844.

Donelson, et al, Bioorganic & Medicinal Chemistry Letters 16:4420-23, (2006).

Elad et al., (1999) Targeting of K-Ras 4B by *S-frans,trans-farnesyl* thiosalicylic acid Biochim. et Biophys. Acta, 1452:228-242.

Gordon et al, "Topical *N*-acetyl-S-farnesyl-L-cysteine Inhibits Mouse Skin Inflammation, and Unlike Dexamethasone, its Effects Are Restricted to the Application Site," *J. Invest. Dermatol.*, 128:643-54 (2008).

Guidance for Industry Nonclinical Studies for the Safety Evaluation of Pharmaceutical Excipients Issued by the US Food and Drug Administration Center for Drug Evaluation and Research, in May 2005.

Haklai et al, (1998) Dislodgment and accelerated degradation of Ras. Biochemistry, 37:1306-1314.

Halaschek-Wiener et al., (2003) "Farnesyl Thiosalicylic Acid Chemosensitizes Human Melanoma In Vivo." *J.* Invest. Dermatol. 120(1):109-15.

Hasne et al., (1999) Characterization of prenylated protein methyltransferase in *Leishmania*. Biochem. J., 342:513-518.

Henriksen et al., (2005) Synthesis of desthio prenylcysteine analogs: sulfur is important for biological activity. Bioorg. Med. Chem. Lett., 15:5080-5083.

Hrycyna et al., (1995) Yeast STE14 methyltransferase, expressed as TrpE-STE14 fusion protein in *Escherichia coli*, for in vitro carboxylmethylation of prenylated polypeptides. Methods Enzymol., 250:251-266.

Huzoor-Akbar et al., (1993) Protein prenylcysteine analog inhibits agonist-receptor-mediated signal transduction in human platelets. Proc. Natl. Acad. Sci. U. S. A., 90:868-872.

Huzoor-Akbar. (1992) Role of protein methylation in agonist-induced signal transduction in human platelets. SAAS Bull. Biochem. Biotechnol., 5:7-12.

International Search Report for PCT/US06/23022 mailed Sep. 21, 2006.

Jonakait et al., (2000) Macrophage cell-conditioned medium promotes cholinergic differentiation of undifferentiated progenitors and synergizes with nerve growth factor action in the developing basal forebrain. Exp. Neurol., 161:285-296.

Katsuki et al., (1998) A potential role of Ras-mediated signal transduction for the enhancement of depolarization-induced Ca2+ responses in hippocampal neurons by basic fibroblast growth factor. Brain Res. Dev. Brain Res., 111:169-176.

Kilic et al., (1997) In Vitro Assay and Characterization of the Farnesylation-dependent Prelamin A Endoprotease, Joumal of Biological Chemistry, 272:8:5298-5304.

Kloog, Y. and Cox, A.D. (2004) Prenyl-binding domains: potential targets for Ras inhibitors and anti-cancer druos. Semin. Cancer Biol., 14:253-261.

Kowluru et al., (1996) Carboxylmethylation of the catalytic subunit of protein phosphatase 2A in insulin-secreting cells: evidence for functional consequences on enzyme activity and insulin secretion Endocrinology, 137:2315-2323.

Kowluru, A. (2000) Evidence for the carboxyl methylation of nuclear lamin-B in the pancreatic beta cell. Biochem. Biophys. Res. Commun., 268:249-254.

Kramer et al., (2003) Isoprenylcysteine carboxyl methyltransferase activity modulates endothelial cell apoptosis. Mol. Biol. Cell, 14:848-857.

Kuehl, F.A., Jr., et al., (1977) "Role of prostaglandin endoperoxide PGG2 in inflammatory processes," Nature, vol. 265, pp. 170-173.

Lamango et al., (2003) Inhibition mechanism of S-adenosylmethionine-induced movement deficits by prenylcysteine analogs Pharmacol. Biochem. Behav., 76:433-442.

Lamango, N.S. (2005) Liver prenylated methylated protein methyl esterase is an organophosphate-sensitive enzyme. J Biochem Mol Toxicol 19:347-357.

Lamango, N.S. and Charlton, C.G. (2000) Famesyl-L-cysteine analogs block SAM-induced Parkinson's disease-like symptoms in rats. Pharmacol Biochem Behav, 66:841-849.

Li, G., Kowluru, A. and Metz, S.A. (1996) Characterization of prenylcysteine methyltransferase in insulin-secreting cells. Biochem. J., 316 ( Pt 1):345-351.

Ma et al., (1994) Mechanistic studies on human platelet isoprenylated protein methyltransferase: farnesylcysteine analogs block platelet aggregation without inhibiting the methyltransferase. Biochemistry, 33:5414-5420.

Marciano et al., (1995) Farnesyl derivatives of rigid carboxylic acidsinhibitors of ras-dependent cell growth. J. Med. Chem., 38:1267-1272.

Marom et al., (1995) Selective inhibition of Ras-dependent cell growth by famesylthiosalisylic acid. J. Biol. Chem., 270:22263-22270.

McLeish et al., (1994) Effect of prenylcysteine analogues on chemoattractant receptor-mediated G protein activation. Cell. Signal., 6:569-579.

Molony et al., (1996) Inhibitors of farnesyl and geranylgeranyl methyltransferases prevent beta 2 integrin-induced actin polymerization without affecting beta 2 integrin-induced Ca2+ signaling in neutrophils. Biochem. Biophys. Res. Commun., 223:612-617.

Mondal et al., (2000) The specific binding of small molecule isoprenoids to rhoGDP dissociation inhibitor (rhoGDI). Biochemistry 39:406-412.

Otsuka et al., (1998) Protein carboxyl methylation controls intracellular pH in human platelets. J. Hypertens., 16:1261-1266.

Papaharalambus et al., (2005) Tumor necrosis factor alpha stimulation of Rac1 activity. Role of isoprenylcysteine carboxylmethyltransferase. J Biol Chem, 280:18790-18796.

Parish et al., (1997) On the mechanism of the inhibition of transducin function by farnesylcysteine analogs. Biochemistry, 36:2686-2693.

Perez-Sala et al., (1991) Methylation and demethylation reactions of guanine nucleotide-binding proteins of retinal rod outer segments, Proc. Natl. Acad. Sci. U. S. A., 88:3043-3046.

Perez-Sala et al., (1992) Prenylated protein methyltransferases do not distinguish between farnesylated and geranylgeranylated substrates. Biochem. J., 284 (Pt 3):835-840.

Perez-Sala et al., (1998) Analogs of farnesylcysteine induce apoptosis in HL-60 cells. FEBS Lett., 426:319-324.

Philips et al., (1993) Carboxyl methylation of Ras-related proteins during signal transduction in neutrophils. Science, 259:977-980.

Philips et al., (1995) Activation-dependent carboxyl methylation of neutrophil G-protein gamma subunit. Proc. Natl. Acad. Sci. U. S. A., 92:2283-2287.

Pillinger et al., (1994) Characterization of a plasma membrane-associated prenylcysteine-directed alpha carboxyl methyltransferase in human neutrophils. J. Biol. Chem., 269:1486-1492.

Rao, T.S., et al., (1993) "Comparitive eveluation of arachidonic acid (AA)- and tetradecanoylphorbol acetate (TPA)-induced dermal inflammation," Inflammation, vol. 17, No. 6, pp. 723-741.

Rosado, J.A., Sage, S.O. (2000) Farnesylcysteine analogues inhibit store-regulated Ca2+ entry in human platelets: evidence for involvement of small GTP-binding proteins and actin cytoskeleton. Biochem J. 347 Pt 1:183-92.

Roullet et al., (1996) Farnesyl analogues inhibit vasoconstriction in animal and human arteries. J. Clin. Invest., 97:2384-2390.

Scheer, A. and Gierschik, P. (1993) Farnesylcysteine analogues inhibit chemotactic peptide receptor-mediated G-protein activation in human HL-60 granulocyte membranes. FEBS Ltt., 319:110-114.

Scheer, A. and Gierschik, P. (1995) S-prenylated cysteine analogues inhibit receptor-mediated G protein activation in native human granulocyte and reconstituted bovine retinal rod outer segment membranes. Biochemistry. 34:4952-4961.

Search Results for N-acetyl-S-trans, trans-farnesyl-L-cysteine, N-acetyl-S-all-trans geranylgeranylcysteine, S-trans, trans-farnesly thiosalicylic acid, S-all-trans-geranylgeranyl thiosalicylic acid, S-trans, tams-farnesylthiopropionate, and S-all-trans-geranlygeranylthiopropionate in the Chemical Abstracts Service Registry, Marpatpreview, Derwent World Patents Index Chemical Resource segment and Beilstein files. Dec. 16, 2004.

Shi, Y.Q. and Rando, R.R. (1992) Kinetic mechanism of isoprenylated protein methyltransferase. J. Biol. Chem., 267:9547-9551.

Tan et al., (1991) Identifying the recognition unit for G protein methylation. J. Biol. Chem., 266:10719-10722.

Trommer and Neubert, "Overcoming the stratum corneum: the modulation of skin penetration. A Review." *Skin Pharmacol. Physiol.*, 19(2):106-21 (Abstract), (2006).

Van Dessel et al., (2002) Prenylcysteine carboxymethyltransferase type III activity is decreased in retinoic acid-treated SH-SY5Y neuroblastoma cells. Int. J. Biochem. Cell Biol., 34:477-486.

Volker et al., (1991) "Effects of Farnesylcysteine Analogs on Protein Carboxyl Methylation and Signal Transduction," The Journal of Biological Chemsitry, vol. 266, No. 32, pp. 21515-21522.

Volker et al., (1991) "Prenylcysteine Analogs to Study Function of Carboxylmethylation in Signal Transduction," Methods Enzymol., vol. 250, pp. 216-225.

Volker et al., (1991) A single activity carboxyl methylates both farnesyl and geranylgeranyl cysteine residues. FEBS Ltt., 295:189-194.

Volker et al., (1995) Prenylcysteine analogs to study function of carboxylmethylation in signal transduction. Methods Enzymol 250:216-225.

Volker, (1995) "Carboxyl Methylation at C-Terminal S-Prenylcysteine Residues," Ph.D. Thesis, Department of Chemistry, Princeton University, Princeton, NJ, 571:1, 441.

Volker, C., and Stock, J.B. (1995) Carboxyl methylation of Ras-related proteins. Methods Enzymol 255:65-82.

Winter-Vann et al., (2003) Targeting Ras signaling through inhibition of carboxyl methylation: an unexpected property of methotrexate. Proc Natl Acad Sci U S A 100:6529-6534.

Winter-Vann et al., (2005) A small-molecule inhibitor of isoprenylcysteine carboxyl methyltransferase with antitumor activity in cancer cells. Proc Natl Acad Sci U S A 102:4336-4341.

Winter-Vann, A.M. and Casey, P.J. (2005) Post-prenylation-processing enzymes as new targets in oncogenesis. Nat Rev Cancer, 5:405-412.

Written Opinion for PCT/US06/23022 mailed Sep. 21, 2006.

Xu et al., (1996) Inhibition of capacitative Ca2+ entry into cells by farnesylcysteine analogs. Mol. Pharmacol., 50:1495-1501.

Yoo et al., (1998) Partial purification of protein farnesyl cysteine carboxyl methyltransferase from bovine brain. Exp. Mol. Med., 30:227-234.

Zhang et al., (1997) Isolation and characterization of a prenylcysteine lyase from bovine brain. J. Biol. Chem., 272:23354-23359.

Zhang, F.L. and Casey, P.J. (1996) Protein prenylation: molecular mechanisms and functional consequences. Annu. Rev. Biochem., 65:241-269.

"Prevent" from dictionary.com, accessed Nov. 28, 2007.

Kotyuk, et al., "Effect of anti-inflammatory compounds on edema formation and myeloperoxidase activity in the arachidonic acid-induced ear model in the mouse," *Agents Actions* 39, Special Conference Issue (1993), Abstract.

Gábor, *Mouse Ear Inflammation Models and their Pharmacological Application*, pp. 5-10 and pp. 28-37, (2002) Akadémiai Kiadó, Budapest, Hungary.

Response to Office Action, filed Aug. 31, 2011 in parent application, U.S. Appl. No. 11/151,174.

Declaration by Dr. Braham Shroot, filed Aug. 31, 2011 in parent application U.S. Appl. No. 11/151,174.

\* cited by examiner

AFC Inhibits TPA induced edema in mouse ear model

B = AFC treated ear.
C = Vehicle treated ear.

Inhibition of contact dermatitis in volunteer

Exposure to 20% SDS in Hilltop Patch

+AFC          -AFC

TOPICAL COMPOSITIONS AND METHODS FOR EPITHELIAL-RELATED CONDITIONS

CROSS REFERENCE TO RELATED APPLICATIONS

This application is a divisional of and claims the benefit of U.S. patent application Ser. No. 11/151,174, filed Jun. 13, 2005, which was published as U.S. Patent Publication No. 2005/0277694 on Dec. 15, 2005. This application and U.S. patent application Ser. No. 11/151,174 claim the benefit of priority of U.S. Provisional Patent Application No. 60/579,093 filed on Jun. 12, 2004. This application and U.S. patent application Ser. No. 11/151,174 also claim the benefit of priority of U.S. Provisional Patent Application No. 60/652,921 filed on Feb. 14, 2005. The entire disclosures of U.S. Provisional Patent Application No. 60/579,093, U.S. Provisional Patent Application No. 60/652,921, and U.S. patent application Ser. No. 11/151,174 are herein incorporated by reference.

FIELD OF THE INVENTION

The present invention relates to pharmaceutical, cosmetic and cosmeceutical topical compositions containing polyisoprenyl-protein inhibitor compounds and methods useful in the promotion of healthy epithelium and the treatment of epithelial-related conditions.

BACKGROUND OF THE INVENTION

Many skin or mucosal membrane conditions or disorders result from inflammation caused by, inter alia bacteria, fungi, viruses, parasites, autoimmune disorders, allergens, environmental conditions, such as extreme temperatures, wounds, hormones and/or malignant agents. Thus, inflammation can be associated with numerous underlying conditions ranging from dry skin to infections to cancer, as well as being symptomatic of inflammatory disorders such as dermatitis.

Inflammation is often characterized by a strong infiltration of leukocytes at the site of inflammation, particularly neutrophils (polymorphonuclear cells). These cells promote tissue damage by releasing toxic substances at the vascular wall or in uninjured tissue.

Neutrophil infiltration results from amplifying cascades of cell-cell communication involving signal transduction proteins such as G-proteins that can facilitate intracellular regulation and intercellular communication by interacting with a wide range of different regulatory receptor-transducer proteins such as membrane-bound receptors. For these interactions to occur, many of the signal transduction proteins, including virtually all G-proteins, must first be modified by the post-translational addition of a C15 farnesyl or C20 geranylgeranyl polyisoprenoid moiety in thioether linkage to a cysteine residue located at or near the carboxy terminus within a so-called CAAX box or related cysteine-containing sequence. Carboxy terminal polyisoprenoid cysteines that ultimately result from these modifications are subject to methylesterification by a specific membrane-associated S-adenosylmethionine-dependent polyisoprenyl-S-cysteinyl methyltransferase. Compounds that can inhibit these enzymatic reactions or otherwise alter the interactions among polyisoprenylated signal transduction proteins, such as G-proteins and the protein regulatory targets with which they interact, or other intracellular signaling proteins, can be used to mitigate leukocyte responses and, theoretically, to treat inflammatory-related conditions. (see e.g. Volker et al., *Methods Enzymol.*, 1995, 250, 216-225)

One such compound is N-acetylfarnesyl-cysteine (AFC). AFC has been shown to inhibit membrane-associated polyisoprenoid methyl transferase and to block some neutrophil, macrophage, and platelet responses in vitro. Unfortunately, AFC requires high concentrations for efficacy and is expected to result in generalized systemic effects and multiple side effects since it interferes with a central cell regulation mechanism, characteristics which would seem to preclude its use in vivo. However, because such inhibitory compounds have the potential to be highly efficacious, there is a need in the art for compositions containing these compounds that can act as a safe and effective antidote for skin and mucosal membrane conditions.

SUMMARY OF THE INVENTION

The invention provides a topical composition for treating or preventing an epithelial condition in a subject, including a human, in need of treatment thereof, that includes at least one polyisoprenyl-protein inhibitor compound and a carrier.

In another embodiment, provided herein is a topical composition for promoting healthy skin in a subject, including a human, that includes at least one polyisoprenyl-protein inhibitor compound and a carrier.

In a further embodiment, the invention provides a topical composition for promoting healthy skin in a subject, including a human, that includes at least one polyisoprenyl-protein inhibitor compound and a carrier.

In another embodiment, provided herein, is a topical pharmaceutical composition for treating or preventing an epithelial condition in a subject, including a human, in need of treatment thereof that includes at least one polyisoprenyl-protein inhibitor compound and a carrier.

In a further embodiment, the invention provides a topical cosmetic composition for treating or preventing an epithelial condition in a subject, including a human, in need of treatment thereof, that includes at least one polyisoprenyl-protein inhibitor compound and a carrier.

In another embodiment, provided herein is a method of treating or preventing an epithelial-related condition, the method including the step of topically applying onto a surface of a mammal, including a human, in need thereof, a pharmaceutically effective amount of a composition including at least one polyisoprenyl-protein inhibitor compound and a carrier.

In a further embodiment, the invention provides a method of treating or preventing an epithelial-related condition, the method including the step of topically applying onto a surface of a subject, including a human, in need thereof, a cosmetically effective amount of a composition that includes at least one polyisoprenyl-protein inhibitor compound and a carrier.

In another embodiment, provided herein is a method of promoting healthy skin in a subject, including a human in need thereof, the method including the step of topically applying onto a surface of a subject, including a human, in need thereof, a pharmaceutically effective amount of a composition that includes at least one polyisoprenyl-protein inhibitor compound; and a carrier.

In a further embodiment, provided herein is a method of promoting healthy skin in a subject, including a human, in need thereof, the method including topically applying onto a surface of a subject, including a human, a cosmetically effective amount of a composition that includes at least one polyisoprenyl-protein inhibitor compound and a carrier.

In another embodiment, the invention provides a method of promoting healthy skin in a subject, including a human in need thereof, the method including topically applying onto a surface a cosmetically effective amount of a composition that includes at least one polyisoprenyl-protein inhibitor compound and a carrier.

Finally, the invention provides a method of preparing a topical composition, the method including the step of admixing at least one polyisoprenyl-protein inhibitor compound and a carrier.

DETAILED DESCRIPTION OF THE INVENTION

Figure 1:
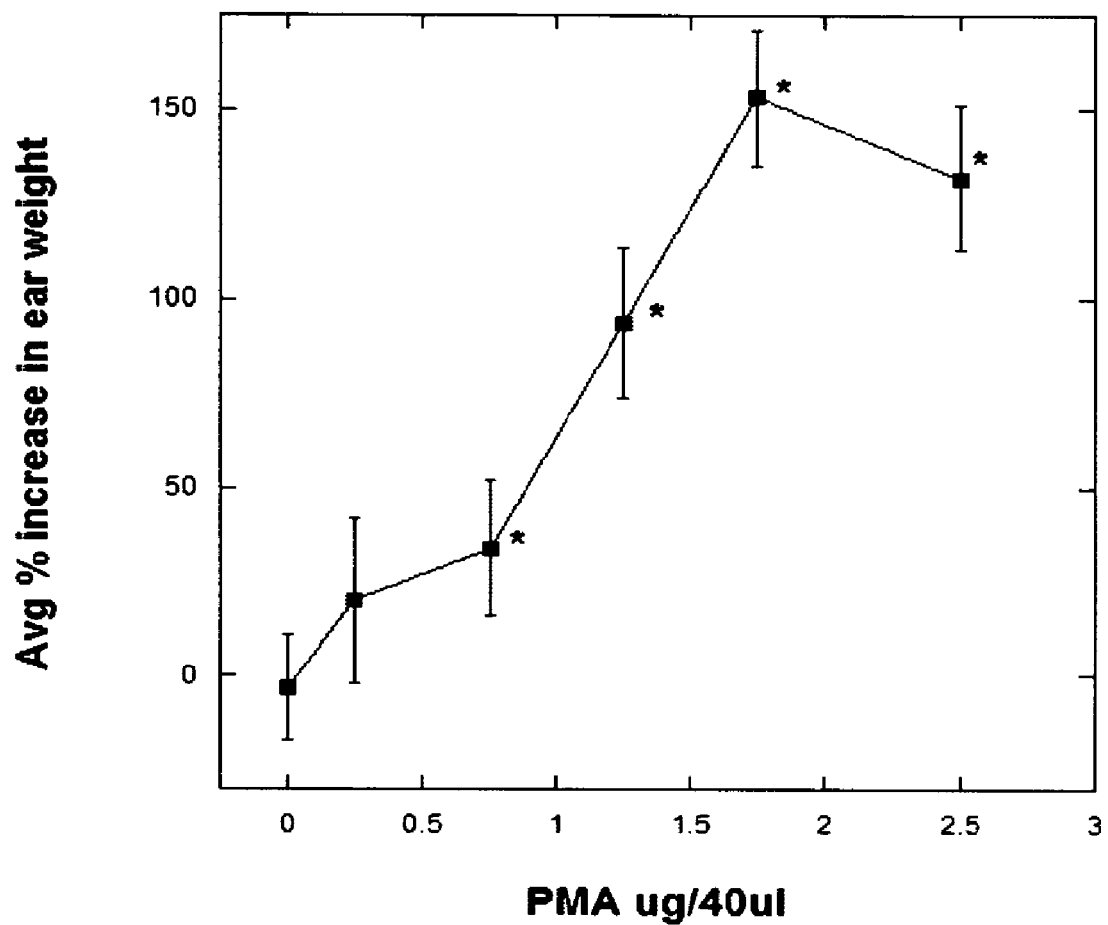
FIG. 1. Induction of edema by TPA
FIG. 2. AFC, alone, does not cause mouse ear edema.

Surprisingly, the inventors have recognized that inventive compositions containing polyisoprenyl-protein inhibitor compounds such as AFC can be used effectively in topical applications to promote healthy epithelia or to treat epithelial-related disorders. These inventive compositions do not exhibit systemic effects when topically applied. Such inventive compositions are useful for, inter alia, their soothing, moisturizing and detergent properties, for treating cosmetic conditions and/or for generally promoting healthy skin. The compositions of the present invention may be usefully employed in cosmetic, cosmeceutical and general skincare compositions as well as in pharmaceutical compositions.

The phrase "epithelia" or "epithelial" or "epithelial tissues" as used throughout the specification and claims is meant to include skin and mucosal membranes. Thus, the present invention offers compositions useful for treating a condition of the skin or a mucosal membrane, such as, but not limited to, that of a nose, a mouth, an eye, an ear, a vagina and a rectum.

The term "topical" refers to administration of an inventive composition at, or immediately beneath, the point of application.

The phrase "topically applying" describes application onto one or more surfaces(s) including epithelial surfaces. "Topically applying" refers to direct application to the area of the surface to be affected. The composition may be applied by pouring, dropping, or spraying, if a liquid; rubbing on, if an ointment, lotion, cream, gel, or the like; dusting, if a powder; spraying, if a liquid or aerosol composition; or by any other appropriate means.

In one embodiment, the composition of the invention is a pharmaceutical composition. As used herein, a "pharmaceutical composition" refers to a composition that is employed to prevent, reduce in intensity, cure or otherwise treat a target condition or disease.

In another embodiment, the composition of the invention is a cosmetic composition. As used herein a "cosmetic composition' refers to a composition that is intended to be rubbed, poured, sprinkled, or sprayed on, introduced into, or otherwise applied to a subject or any part thereof for cleansing, beautifying, promoting attractiveness, or altering the appearance, or an article intended for use as a component of any such article, except that such term does not include soap.

In another embodiment, the composition of the invention is a cosmeceutical composition. As used herein the term "cosmeceutical composition" refers to a composition that is employed as both a cosmetic composition and as a pharmaceutical composition.

In another embodiment, the composition includes one or more polyisoprenyl-protein inhibitor compounds and a carrier.

As used herein "polyisoprenyl-protein inhibitor compound" refers to a compound that can inhibit or reduce the activity of a polyisoprenylated protein such as a G-protein. As used herein a "G-protein" refers to heterotrimeric G-proteins that associate with receptors of the seven transmembrane domain superfamily and are involved in signal transduction and the small GTP-binding signal transduction proteins that act to regulate cellular processes, including but not limited to cytoskeletal organization, secretion and any other protein that is subject to polyisoprenylation, such as, but not limited to, arrestin and nuclear laminar proteins.

Without being limited by theory, compounds known in the art to inhibit or reduce G-protein signal transducing activity act by, inter alia, effecting the ability of a G-protein to bind to an interacting regulatory target protein that is frequently, although not always, located in a cellular membrane. In order to interact with these regulatory target proteins, G proteins and related polyisoprenylated proteins undergo several post-translational modifications including covalent attachment of a farnesyl or geranylgeranyl moiety in thioether linkage to cysteine residues located at or in close proximity to their carboxy termini and methylesterification of exposed terminal farnesyl- or geranylgeranyl-S-cysteinyl residues.

Inflammatory agonists stimulate the methylesterification of polyisoprenyl-S-cysteinyl residues of some G-proteins (Volker et al., *Methods Enzymol.*, 1995, 250, 216-225). Agents that inhibit this methylesterification reaction inhibit G-protein-mediated inflammatory responses. Consequently, it is believed that polyisoprenyl-S-cysteine carboxyl methyltransferase inhibitors may serve as anti-inflammatory agents (Volker et al., *Methods Enzymol.*, 1995, 250, 216-225).

Other preferred mechanisms for G-protein inhibition are discussed in Volker, C., Miller, R. A., McCleary, W. R., Rao, A., Poenie, M., Backer, J. M., and Stock, J. B. (1991), *Effects of farnesylcysteine analogs on protein carboxyl methylation and signal transduction*. J. Biol. Chem. 266, 21515-21522, herein incorporated by reference.

Non-limiting examples of polyisoprenyl-protein inhibitor compounds for use in the composition of the present invention are described in U.S. Pat. No. 5,043,268 issued Aug. 27, 1992 to Jeffry B. Stock; U.S. Pat. No. 5,202,456, issued Apr. 13, 1993 to Robert R. Rando; U.S. Pat. No. 5,705,528 issued Jan. 6, 1998 to Yoel Kloog; U.S. Pat. No. 6,096,740 issued Aug. 1, 2000 to Mechoulam, et al.; U.S. Pat. No. 5,521,215 issued May 28, 1996 to Mechoulam; U.S. Pat. No. 5,284,867 issued Feb. 8, 1994 to Mechoulam; U.S. Pat. No. 6,482,086 to Kloog issued Oct. 8, 2002; U.S. Patent Application 2003/0203942A1 published Oct. 30, 2003; U.S. Pat. No. 6,372,793 issued Apr. 6, 2002 to Nazarius S. Lamango and J. Invest. Dermatol. 2003 January; 120(1):109-15 by Halaschek-Wiener, et al. Each of these references is incorporated by reference herein. Other compounds include cannabinoids such as Δ-tetrahydrocannabinol (THC) and cannabidiol; certain unsaturated fatty acids such as linoleic acids and omega-3 fatty acids. Additional useful polyisoprenyl-protein s can be found in Volker, C. R. 1995. Carboxyl Methylation at C-terminal S-prenylcysteine residues. Ph.D. thesis, Princeton University, Princeton, N.J. It should be understood that analogs of these compounds that show this inhibitor activity are also useful, as are compounds having different structural characteristics than those described.

In one embodiment, preferred compounds include those set forth in U.S. Pat. No. 5,043,268 represented by Formula (I) and derivatives thereof.

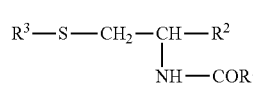
(I)

Wherein:
$R^1$ is alkyl of 1 to 3 carbon atoms;
$R^2$ is —COX; wherein X is —OH, —OCH$_3$, —NH$_2$, —NHR$^4$, —N(R$^4$)$_2$ or halogen;
$R^3$ is a straight or branched chain alkyl of 10 to 25 carbon atoms, a straight or branched chain alkenyl, including a polyunsaturated alkenyl, of 10 to 25 carbon atoms;
$R^4$ is an alkyl at least 1 to about 25 carbon atoms; and
the pharmaceutically-acceptable salts and esters of these compounds thereof.

As used herein the term a "pharmaceutically-acceptable salt" refers to salts generally that are prepared by reacting a free base with a suitable organic or inorganic acid or by reacting an acid with a suitable organic or inorganic base, wherein a basic group or an acidic group is present in the compound of the inventive composition.

As used herein, the term "alkyl" refers to a straight or branched chain hydrocarbon, optionally substituted with lower alkyl or cycloalkyl substituents, with multiple degrees of substitution being allowed. As used herein, "cycloalkyl" refers to an alicyclic hydrocarbon group optionally possessing one or more degrees of unsaturation, having from three to twelve carbon atoms, optionally substituted with nitrogen, oxygen, or sulfur. "Cycloalkyl" includes by way of example cyclopropyl, cyclobutyl, cyclopentyl, cyclohexyl, cycloheptyl or cyclooctyl, and the like The term "straight or branched chain alkyl" as used for $R^3$ denotes groups including decyl, undecyl, dodedecyl, octadecyl, nonadecyl, eicosyl, heneicosyl, decosyl, tricosyl, tetracosyl, pentacosyl, and the branched isomers thereof.

The term "straight or branched chain alkenyl" refers to a hydrocarbon moiety having at least one carbon-carbon double bond, which can be optionally substituted with a nitrogen-carbon double bond (including polyunsaturated alkenyl). Alkenyl as used herein for $R^3$ denotes groups including decenyl, undecenyl, dodecenyl, heptadecenyl, octadecenyl, nonadecenyl, eicosenyl, heneicosenyl, docosenyl, tricosenyl, tetracosenyl, pentacosenyl, the branched chain isomers thereof, and polyunsaturated alkenes including octadec-9,12-dienyl, octadec-9,12,15-trienyl, and eicos-5,8,11,14-tetraenyl.

In a preferred embodiment, $R^2$ is —COOH. When $R^2$ is —COOH, the alkali metal, alkaline earth metal, ammonium, and substituted ammonium salts thereof are desired.

In another preferred embodiment, $R^1$ is methyl. In yet another preferred embodiment, $R^3$ is farnesyl.

Even more preferably, $R^1$ is methyl, $R^2$ is COOH, and $R^3$ is farnesyl.

In yet another preferred embodiment, $R^1$ is methyl, X is —OCH$_3$, and $R^3$ is farnesyl.

In another embodiment, the composition of the invention includes those compounds selected from Formula II or Formula III as set forth in U.S. Pat. No. 5,202,456.

or

wherein W is a farnesyl group, a geranylgeranyl group, a substituted farnesyl group or a substituted geranylgeranyl group; Y is:

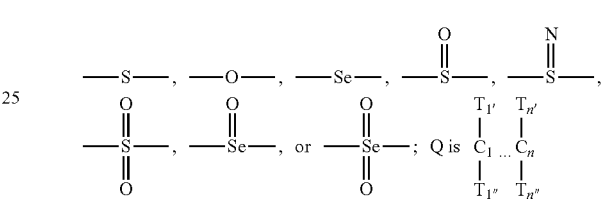

wherein n=1, 2, 3, 4, 5, or 6. It is understood that $C_1 \ldots C_n$ represents 1 to 6 carbons and that when there are two or more carbons, they are connected in a linear chain by covalent bonds. The covalent bonds may be single, double, or triple bonds. When there are three or more carbons the bonds do not all have to be of the same type. For example, $C_1$ may be attached to $C_2$ by a single bond, and $C_2$ may be attached to $C_3$ by a double bond. When double or triple bonds are present, two or more of $T_{1'} \ldots T_{n'}$ and $T_{1''} \ldots T_{n''}$ are eliminated. Each of $T_{1'} \ldots T_{n'}$ and $T_{1''} \ldots T_{n''}$ is independently: H, Fl, Br, —NHCOCH$_3$, —NH$_2$, a peptide (preferably linked to $C_n$ by an amide bond; preferably of 10 or fewer amino acids), an alkene group (preferably linked to $C_n$ by an amide bond; preferably of 20 or fewer carbons), a polyetheleneglycol group (preferably linked to $C_n$ by an amide bond), a saturated fatty acid (preferably linked to $C_n$ by an amide bond; preferably of 20 or fewer carbons), or an unsaturated fatty acid (preferably linked to $C_n$ through an amide bond; preferably of 20 or fewer carbons), a monosaccharide (preferably attached to $C_n$ through carbon or oxygen), or a disaccharide (preferably attached to $C_n$ through carbon or oxygen); and Z is —COOH or salts or esters (e.g. methyl, ethyl, or propyl esters) thereof. Esters of —COOH, —PO$_3$, or —SO$_3$ are preferred to the free acid because they are more readily taken up by cells. Many cells have esterases which can regenerate the free acid, which is in some cases preferred.

Regarding the farnesyl and geranylgeranyl moieties, hydrogen generally may be replaced by fluorine, and a methyl group may generally be replaced by a bromine. Accordingly, "substituted farnesyl group" means a farnesyl moiety in which one or more hydrogens have been replaced by fluorine or one or more methyl groups have been replaced by a bromine, and "substituted geranylgeranyl group" means a geranylgeranyl moiety in which one or more hydrogens have been replaced by fluorine or one or more methyl groups have been replaced by bromine. In addition, the C=C double bonds in the farnesyl or geranylgeranyl groups may be replaced by single bonds with the concurrent addition of hydrogens and/or halogens to the participating carbons.

In a preferred embodiment, the compounds for use in the composition of the invention are S-farnesylcysteine, N-acetyl-S-geranylcysteine, N-acetyl-S-farnesylcysteine ("AFC"), also referred to as N-acetyl-S-trans, trans-farnesyl-L-cysteine, N-acetyl-S-geranylgeranylcysteine ("AGGC"), S-farnesyl-2-mercaptoethanesulfonic acid, S-farnesylthioacetic acid, S-farnesylmercaptosuccinic acid, S-farnesylthiotriazole, S-farnesylthiosalicylic acid ("FTS"), S-farnesylthiosuccinic acid, 2-chloro-5-farnesylaminobenzoic acid, 2-farnesyl-thionicotinic acid ("FTN"), 5-fluoro-FTS, 5-chloro-FTS, 4-chloro-FTS, S-farnesyl-methylthiosalicylic acid or combinations thereof.

In a more preferred embodiment, the inventive compositions contain one or more of farnesylcysteine, N-acetylgeranylcysteine, N-acetylfarnesylcysteine ("AFC"), N-acetylgeranylgeranylcysteine ("AGGC"), farnesyl-2-mercaptoethanesulfonic acid, farnesylthioacetic acid, farnesylmercaptosuccinic acid, farnesylthiotriazole, farnesylthiosuccinic acid, farnesyl-thiosalicylic acid ("FTS"), 2-chloro-5-farnesylaminobenzoic acid, 2-farnesyl-thionicotinic acid ("FTN"), 5-fluoro-FTS, 5-chloro-FTS, 4-chloro-FTS, and S-farnesyl-methylthiosalicylic acid.

In another preferred embodiment, AGGC and AFC are used in combination.

In a more preferred embodiment, AFC is used in the inventive composition.

In another embodiment, two or more polyisoprenyl-protein inhibitor compounds are used in the inventive composition to obtain a specific pharmaceutical or cosmetic effect.

In one embodiment, polyisoprenyl-protein inhibitor compounds prevent post-translational carboxyl methylation.

In another embodiment of the present invention, polyisoprenyl-protein inhibitor compounds act by inhibiting polyisoprenyl cysteine methyltransferase.

In another embodiment, the polyisoprenyl-protein inhibitor compound is contained within a botanical extract. Botanical extracts may be assayed for polyisoprenyl-protein inhibitor activity by using the methods described in the example section below. As used herein a "botanical extract" refers to a fresh or processed (e.g. cleaned, frozen, dried, sliced, liquified) part of a single species of plant or a fresh or processed alga or macroscopic fungus.

In another embodiment, the polyisoprenyl-protein inhibitor compound is contained within a bacterial extract. Bacterial extracts likewise can be assayed for polyisoprenyl-protein inhibitor activity according to the methods described in herein.

In another aspect of the present invention, the composition of the present invention includes a carrier. As used herein "carrier" describes a material that does not abrogate the biological activity and properties of the polyisoprenyl-protein inhibitor compound of the composition of the present invention. Carriers must be of sufficiently high purity and of sufficiently low toxicity to render them suitable for administration to the mammal being treated. The carrier can be inert, or it can possess pharmaceutical benefits, cosmetic benefits or both.

Some non-limiting representative examples of carriers include moisturizing agents or humectants, pH adjusting agents, a deodorant agent, fragrances, hair conditioning agents, chelating agents, preservatives, emulsifiers, thickeners, solubilizing agents, penetration enhancers, anti-irritants, colorants and surfactants.

As used herein a "moisturizing agent" is a substance that adds or restores moisture to the skin. Representative examples of moisturizing or humectant agents that are usable in the present invention include, without limitation, guanidine, glycolic acid and glycolate salts (e.g. ammonium salt and quaternary alkyl ammonium salt), aloe vera in any of its variety of forms (e.g., aloe vera gel), allantoin, urazole, polyhydroxy alcohols such as sorbitol, glycerol, hexanetriol, propylene glycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

As is widely recognized in the art, since the pH of the skin is 5.5, compositions for topical skin application (to avoid irritation) should preferably have a pH value of between 4.0 and 7.0, preferably between 5.0 and 6.0, most preferably about 5.5 or substantially 5.5. Hence, a pH adjusting composition is typically added to bring the pH of the composition to the desired value. The compositions of the present invention therefore preferably are formulated to have a pH value that ranges between about 4.0 and about 7.0, more preferably between about 5.0 and about 6.0.

Suitable pH adjusting agents include, for example, but are not limited to, one or more adipic acids, glycines, citric acids, calcium hydroxides, magnesium aluminometasilicates, buffers or any combinations thereof.

As used herein "deodorant agent" refers to a substance for inhibiting or masking perspiration or other bodily odors. Representative examples of deodorant agents that are usable in the context of the present invention include, without limitation, quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmIthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above. Antiperspirant agents can be incorporated in the compositions of the present invention either in a solubilized or a particulate form and include, for example, aluminum or zirconium astringent salts or complexes.

As used herein "fragrance" refers to a substance having a pleasant aroma. Suitable fragrances include, but are not limited to, eucalyptus oil, camphor synthetic, peppermint oil, clove oil, lavender, chamomile and the like.

Suitable hair conditioning agents that can be used in the context of the present invention include, for example, one or more collagens, cationic surfactants, modified silicones, proteins, keratins, dimethicone polyols, quaternary ammonium compounds, halogenated quaternary ammonium compounds, alkoxylated carboxylic acids, alkoxylated alcohols, alkoxylated amides, sorbitan derivatives, esters, polymeric ethers, glyceryl esters, or any combinations thereof.

Chelating agents are optionally added to the compositions of the present invention so as to enhance the preservative or preservative system. Preferred chelating agents are mild agents, such as, for example, ethylenediaminetetraacetic acid (EDTA), EDTA derivatives, or any combination thereof.

Suitable preservatives for use in the compositions of the present composition include, without limitation, one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof.

"Emulsifiers" as used herein promote the formation and stabilization of an emulsion. Suitable emulsifiers may be natural materials, finely divided solids, or synthetic materials. Natural emulsifying agents may be derived from either animal or vegetable sources. Those from animal sources include gelatin, egg yolk, casein, wool fat, or cholesterol. Those from vegetable sources include acacia, tragacanth, chondrus, or pectin. Vegetable sources specifically from cellulose derivatives include methyl cellulose and carboxymethyl cellulose to increase the viscosity. Finely divided emulsifiers include bentonite, magnesium hydroxide, aluminum hydroxide, or magnesium trisylicate. Synthetic agents include anionic, cationic or nonionic agents. Particularly useful are sodium lauryl sulfate, benzalkonium chloride or polyethylene glycol 400 monostearate, or any combinations thereof.

"Thickeners" as used herein refer to agents that make the composition of the present invention dense or viscous in consistency. Suitable thickeners that can be used in the context of the present invention include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids, anionic polymers, and their alkali salts and mixtures thereof.

As used herein "solubilizing agents" are those substances that enable solutes to dissolve. Representative examples of solubilizing agents that are usable in the context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEEN® and spans, e.g., TWEEN 80®. Other solubilizers that are usable for the compositions of the present invention are, for example, polyoxyethylene sorbitan fatty acid ester, polyoxyethylene n-alkyl ethers, n-alkyl amine n-oxides, polyoxamers, organic solvents, such as acetone, phospholipids and cyclodextrin.

A "penetration enhancer" is an agent known to accelerate the delivery of a substance through the skin. Suitable penetration enhancers usable in the present invention include, but are not limited to, dimethylsulfoxide (DMSO), dimethyl formamide (DMF), allantoin, urazole, N,N-dimethylacetamide (DMA), decylmethylsulfoxide ($C_{10}$MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil. Such oils include, for example, safflower oil, cottonseed oil and corn oil.

Additional thickeners, penetration enhancers and other adjuvants may generally be found in *Remington's Pharmaceutical Sciences*, $18^{th}$ or $19^{th}$ editions, published by the Mack Publishing Company of Easton, Pa. which is incorporated herein by reference.

As used herein, an "anti-irritant" is an agent that prevents or reduces soreness, roughness, or inflammation of a bodily part. Suitable anti-irritants that can be used in the context of the present invention include, for example, steroidal and non steroidal anti-inflammatory agents or other materials such as aloe vera, chamomile, alpha-bisabolol, cola nitida extract, green tea extract, tea tree oil, licoric extract, allantoin, caffeine or other xanthines, glycyrrhizic acid and its derivatives.

The presently known anti-irritants can be divided into water-soluble anti-irritants and water-insoluble anti-irritants. Representative examples of such compositions are described, for example, in U.S. Pat. No. 5,482,710 which is herein incorporated by reference.

Colorants may also be used in the compositions of the invention. Colorants include pigments or dyes or a combination thereof as the cosmetic benefit requires. Preferred pigments include, but are not limited to, iron oxides, and titanium oxides. Suitable dyes include FD&C approved colorants, D&C approved colorants, and those approved for use in Europe and Japan. See Marmion, D. M., Handbook of US Colorants for Food, Drugs, Cosmetics, and Medical Devices, 3rd ed, 1991 herein incorporated by reference.

"Surfactants" as used herein are surface-active substances, such as a detergent. Suitable surfactants for use with the inventive compositions include, but are not limited to, sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isothionates, glycerylether sulfonates, sulfosuccinates and combinations thereof. More preferably, the anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

In another embodiment, the inventive compositions are incorporated into a carrier which may be in the form of a mouthwash, rinse, oral spray, suspension, dental gel, and the like. Typical oral carriers known in the art may be used in the present invention. The preferred pharmaceutical and/or cosmetic carriers are water, ethanol, and water-ethanol mixtures. The water-ethanol mixtures are generally employed in a weight ratio from about 1:1 to about 20:1, preferably from about 3:1 to about 20:1, and most preferably from about 3:1 to about 10:1, respectively. The pH value of the oral vehicle is generally from about 4 to about 7, and preferably from about 5 to about 6.5. An oral topical vehicle having a pH value below about 4 is generally irritating to the oral cavity and an oral vehicle having a pH value greater than about 7 generally results in an unpleasant mouth feel.

The oral topical inventive compositions may also contain conventional additives normally employed in those products. Conventional additives include a fluorine providing compound, a sweetening agent, a coloring agent, a humectant, a pH adjusting agent, and an emulsifier, providing the additives do not interfere with the therapeutic or cosmetically beneficial properties of the inventive compositions.

The coloring agents, humectants, pH adjusting agents and emulsifiers set out above as useful in the non-oral topical inventive compositions may be used in the oral inventive composition.

Fluorine providing compounds may be fully or slightly water soluble and are characterized by their ability to release fluoride ions or fluoride containing ions in water and by their lack of reaction with other components in the composition. Typical fluorine providing compounds are inorganic fluoride salts such as water-soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and di-fluorophosphates and fluorinated sodium calcium pyrophosphate. Alkali metal fluorides, tin fluoride and monofluorophosphates, such as sodium and stannous fluoride, sodium monofluorophosphate and mixtures thereof, are preferred.

The amount of fluorine providing compound present in the present oral topical inventive compositions is dependent upon the type of fluorine providing compound employed, the solubility of the fluorine compound, and the nature of the final oral inventive composition. The amount of fluorine providing compound used must be a nontoxic amount. In general, the fluorine providing compound when used will be present in an amount up to about 1%, preferably from about 0.001% to about 0.1%, and most preferably from about 0.001% to about 0.05%, by weight of the oral topical inventive composition.

When sweetening agents (sweeteners) are used, those sweeteners well known in the art, including both natural and artificial sweeteners, may be employed. The sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof.

In a preferred embodiment, a pharmaceutically acceptable carrier is included in the composition. As used herein "a pharmaceutically acceptable carrier" is any substantially non-toxic carrier conventionally useable for topical administration of pharmaceuticals in which the polyisoprenyl-protein inhibitor compound will remain stable and bioavailable when applied directly to skin or mucosal surfaces In another, preferred, embodiment, the compositions of the present invention include a cosmetically acceptable carrier. As used herein the phrase "cosmetically acceptable carrier" refers to a substantially non-toxic carrier, conventionally useable for the topical administration of cosmetics, with which polyisoprenyl-protein inhibitor compounds will remain stable and bioavailable. It will be understood that cosmetically acceptable carriers and pharmaceutically acceptable carriers are similar, if not often identical, in nature.

Suitable pharmaceutically acceptable carriers include water, petroleum jelly (Vaseline™), petroleum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, alcohols, polyols, and the like. Also included are the carriers described hereinabove.

In another embodiment, the pharmaceutically acceptable carrier of the composition of the present invention includes a sustained release or delayed release carrier. The carrier can be any material capable of sustained or delayed release of the polyisoprenyl-protein inhibitor compound to provide a more efficient administration resulting in less frequent and/or decreased dosage of the polyisoprenyl-protein inhibitor compound, ease of handling, and extended or delayed effects on epithelial-related conditions. Non-limiting examples of such carriers include liposomes, microsponges, microspheres, or microcapsules of natural and synthetic polymers and the like. Liposomes which may enhance the localized delivery of the compounds of the inventive composition within skin layers, may be formed from a variety of phospholipids, such as cholesterol, stearylamines or phosphatidylcholines.

Suitable cosmetically acceptable carriers are described in the CTFA International Cosmetic Ingredient Dictionary and Handbook, 8th edition, edited by Wenninger and Canterbery, (The Cosmetic, Toiletry, and Fragrance Association, Inc., Washington, D.C., 2000), which is herein incorporated by reference. Also included are the carriers described hereinabove.

In another embodiment, the compositions of the present invention can further include one or more additional compatible active ingredients which are aimed at providing the composition with another pharmaceutical, cosmeceutical or cosmetic effect, in addition to that provided by a polyisoprenyl-protein inhibitor compound of the inventive composition. "Compatible" as used herein means that the components of such a composition are capable of being combined with each other in a manner such that there is no interaction that would substantially reduce the efficacy of the composition under ordinary use conditions.

In one embodiment, the polyisoprenyl-protein inhibitor compound of the inventive compositions is an active ingredient.

As used herein, the phrase "additional active ingredient" refers to an agent, other than a polyisoprenyl-protein inhibitor compound of the inventive composition, that exerts a pharmacological, dermatological or any other beneficial activity. It is to be understood that "other beneficial activity" may be one that is only perceived as such by the subject using the inventive compositions.

In another embodiment, the polyisoprenyl-protein inhibitor compound of the inventive composition is a new excipient. As used herein a "new excipient" means any inactive ingredient that is intentionally added to the composition of the present invention and is not intended to exert therapeutic effects at the intended dosage, although it may act to improve product delivery. A new excipient is not fully qualified by existing safety data with respect to the currently proposed level of exposure, duration of exposure or route of administration. Additional characteristics of new excipients can be found in the Guidance for Industry Nonclinical Studies for the Safety Evaluation of Pharmaceutical Excipients issued by the US Food and Drug Administration Center for Drug Evaluation and Research, in May, 2005, herein incorporated by reference.

Compositions according to the present invention, which further include one or more additional active ingredients, can therefore be further efficiently used, in addition to their use as a treatment for an epithelial-related condition, in the treatment of any medical, cosmetic and/or cosmeceutical condition in which applying the additional active ingredient is beneficial.

Preferred additional active ingredients according to the present invention include, without limitation, one or more, in any combination, of a protective agent, an emollient, an astringent, an irritant, a keratolytic, a sun screening agent, a sun tanning agent, an antibiotic agent, an antifungal agent, an antiviral agent, an antiprotozoal agent, an anti-acne agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, a hormone, an anti-dandruff agent, an anti-wrinkle agent, an anti-skin atrophy agent, a sclerosing agent, a cleansing agent, a caustic agent and a hypo-pigmenting agent.

In the broadest pharmacological sense, a "protective" is any agent that isolates the exposed surface of the skin or other membrane from harmful or annoying stimuli. Protectives as described herein may take the form of dusting powders, adsorbents, mechanical protective agents, and plasters. Dusting powders are relatively inert and insoluble materials that are used to cover and protect epithelial surfaces, ulcers and wounds. Usually, these substances are finely subdivided powders that absorb moisture and can act as a dessicant. The absorption of skin moisture decreases friction and also discourages certain bacterial growth. Some of the materials used as protective adsorbents include bentonite, insoluble salts of bismuth, boric acid, calcium carbonate, (precipitated), cellulose, corn starch, magnesium stearate, talc, titanium dioxide, zinc oxide, and zinc stearate.

Protectives also can be administered to the skin to form an adherent, continuous film that may be flexible or semi-rigid depending on the materials and the formulations as well as the manner in which they are applied. This material may serve several purposes including providing occlusion from the external environment, providing chemical support, and serving as vehicles for other medicaments. Mechanical protectives are generally either collodions or plasters. Examples include aluminum hydroxide gel, collodium, dimethicone, petrolatum gauze, absorbable gelatin film, absorbable gelatin sponge, zinc gelatin, kaolin, lanolin, anhydrous lanolin, mineral oil, mineral oil emulsion, mineral oil light, olive oil, peanut oil, petrolatum, silicones, hydrocolloids and the like.

Preferably, protectives included in the composition of the invention are demulcents. Demulcents are protective agents employed primarily to alleviate irritation, particularly mucous membranes or abraded tissues. They often are applied to the surface in a viscid, sticky preparation that covers the area readily and may be medicated. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

"Emollients" are generally bland, fatty or oleaginous materials which can be applied locally, particularly to the skin. Emollients increase the tissue moisture content, thereby rendering the skin softer and more pliable. Increased moisture content in the skin can be achieved by preventing water loss with an occlusive water-immiscible barrier, by increasing the water-holding capacity in the skin with humectants, or by altering the desquamation of the outermost skin layer, the stratum corneum. Useful emollients include lanolin, spermaceti, mineral oil, paraffin, petrolatum, white ointment, white petroleum, yellow ointment. Also included are vegetable oils, waxes, cetyl alcohol, glycerin, hydrophilic petrolatum, isopropyl myristate, myristyl alcohol, and oleyl alcohol.

"Astringents" are locally applied, generally protein precipitants, that have such a low cell penetrability that the action essentially is limited to the cell surface and interstitial spaces. The astringent action is accompanied by contraction and wrinkling of the tissue and by blanching. Astringents are used therapeutically to arrest hemorrhage by coagulating the blood, to promote healing, to toughen the skin or to decrease sweating. The principal components of astringents are salts of aluminum, zinc, manganese, iron or bismuth.

An "irritant" is a material that acts locally on the skin to induce, based on irritant concentration, hyperemia, inflammation, and desiccation. Irritant agents include, but are not limited to, alcohol, aromatic ammonia spirits, benzoin tincture, camphor capsicum, and coal tar extracts. Preferably, the irritant is a rubefacient. As used herein "rubefacients" are agents that induce hyperemia, wherein hyperemia means an increased amount of blood in a body part or organ. Rubefaction, which is induced by rubefacients, results from increased circulation to an injured area and is accompanied by a feeling of comfort, warmth, itching and hyperesthesia.

"Keratolytics" (desquamating agents) act to remove outer layers of the stratum corneum. This is particularly useful in hyperkeratotic areas. The keratolytics include benzoyl peroxide, fluorouracil, resorcinol, salicylic acid, tretinoin, and the like.

Representative examples of sun screening agents usable in context of the present invention include, without limitation, p-aminobenzoic acid and its salts and derivatives thereof (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propylene glycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzylacetone and benzylacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene boman-2-one) and 4-isopropyl-di-benzoylmethane, and any combination thereof.

Representative examples of sunless tanning agents usable in the present invention include, without limitation, dihydroxyacetone, glyceraldehyde, indoles and their derivatives. The sunless tanning agents can be used in combination with the sunscreen agents.

The term "antibiotic agent" as used herein means any of a group of chemical substances having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

The term "anti-fungal agent" as used herein means any of a group of chemical substances having the capacity to inhibit the growth of or to destroy fungi. Anti-fungal agents include but are not limited to Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

The term "anti-viral agent" as used herein means any of a group of chemical substances having the capacity to inhibit the replication of or to destroy viruses used chiefly in the treatment of viral diseases. Anti-viral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetylleucine, Amantadine, Amidinomycin, Delavirdine, Foscamet, Indinavir, Interferon-α, Interferon-β, Interferon-γ, Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, Zidovudine (AZT) and Xenazoic Acid.

The term "anti-protozoal agent" as used herein means any of a group of chemical substances having the capacity to inhibit the growth of or to destroy protozoans used chiefly in the treatment of protozoal diseases. Examples of antiprotozoal agents, without limitation include pyrimethamine (Daraprim®) sulfadiazine, and Leucovorin.

Suitable anti-acne agents of the present invention include, without limitation, keratolytics, such as salicylic acid, sulfur, glycolic, pyruvic acid, resorcinol, and N-acetylcysteine; and retinoids such as retinoic acid and its derivatives (e.g., cis and trans, esters).

"Anesthetic agents" refers to agents that resulting in a reduction or loss of sensation. Non-limiting examples of anesthetic drugs that are suitable for use in the context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

"Steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasonephosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

"Non-steroidal anti-inflammatory agents" refers to a large group of agents that are aspirin-like in their action, including ibuprofen (Advil)®, naproxen sodium (Aleve)®, and acetaminophen (Tylenol)®. Additional examples of non-steroidal anti-inflammatory agents that are usable in the context of the present invention include, without limitation, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

"Antipruritic agents" as used herein refers to those substances that reduce, eliminate or prevent itching. Suitable antipruritic agents include, without limitation, pharmaceutically acceptable salts of methdilazine and trimeprazine.

"An anti-oxidant agent" as used herein refers to a substance that inhibits oxidation or reactions promoted by oxygen or peroxides. Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

"Chemotherapetic agent" refers to chemicals useful in the treatment or control of a disease. Non-limiting examples of chemotherapeutic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

"Antihistamine agent" as used herein refers to any of various compounds that counteract histamine in the body and that are used for treating allergic reactions (such as hay fever) and cold symptoms. Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

"Vitamin" as used herein, refers to any of various organic substances essential in minute quantities to the nutrition of most animals act especially as coenzymes and precursors of coenzymes in the regulation of metabolic processes. Non-limiting examples of vitamins usable in context of the present invention include vitamin A and its analogs and derivatives: retinol, retinal, retinyl palmitate, retinoic acid, tretinoin, isotretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

"Hormone" as used herein refers to natural substances produced by organs of the body that travel by blood to trigger activity in other locations or their synthetic analogs. Suitable hormones for use in the context of the present invention include, but are not limited to, calciferol (Vitamin $D_3$) and its products, androgens, estrogens and progesterones.

"Anti-dandruff agents" as used herein refer to agents that reduce, eliminate or prevent a scurf from forming on skin, especially of the scalp, that comes off in small white or grayish scales. Exemplary anti-dandruff ingredients usable in context of the present invention include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopiroxolamine, and mixtures thereof.

"Anti-skin atrophy actives" refers to substances effective in replenishing or rejuvenating the epidermal layer by promoting or maintaining the natural process of desquamation. Examples of antiwrinkle and antiskin atrophy actives which can be used in context of the present invention include retinoic acid its prodrugs and its derivatives (e.g., cis and trans) and analogues; salicylic acid and derivatives thereof, sulfur-containing D and L amino acids and their derivatives and salts, particularly the N-acetyl derivatives, a preferred example of which is N-acetyl L-cysteine; thiols, e.g. ethane thiol; alpha-hydroxy acids, e.g. glycolic acid, and lactic acid; phytic acid, lipoic acid; lysophosphatidic acid, and skin peel agents (e.g., phenol and the like). Sclerosing agents or sclerosants may be also employed. A "sclerosant" refers to an agent used as a chemical irritant injected into a vein in sclerotherapy. The most common ones are morrhuate sodium, sodium tetradecyl sulfate, laureth 9 and ethanolamine oleate.

Cleansing agents which may be use in the present invention include surfactant based cleansing agents, examples of which have been listed hereinabove. Other non-surfactant-based cleansing agents known to those of skill in the art may also be employed.

"Caustic agents" refer to substances capable of destroying or eating away epithelial tissue by chemical action. Caustic agents can be used to remove dead skin cells. For example, beta-hydroxy acids, naturally derived acids with a strong kerolytic effect, are useful for problem skin, acne or peeling.

"Hypopigmenting agents" refer to substances capable of depigmenting the skin. Suitable hypopigmenting agents include hydroquinones, mequinol, and various protease inhibitors including serine protease inhibitors, active soy and retinoic acid.

The topical compositions of the present invention can be applied locally to the skin or mucosa and may be in any form including solutions, oils, creams, ointments, gels, lotions, shampoos, milks, cleansers, moisturizers, sprays, skin patches and the like.

In another embodiment, a polyisoprenyl-protein inhibitor compound, carrier and, optionally, additional active ingredients are formed into a composition comprising a solution, emulsion or gel suspension.

In some embodiments, a polyisoprenyl-protein inhibitor compound, a pharmaceutical or cosmetic carrier and, optionally, one or more additional active ingredients are in the form of a solution. A solution can be prepared by mixing a solute or dissolved substance (such as a polyisoprenyl-protein inhibitor compound of the invention and, optionally, one or more active ingredient(s)) uniformly throughout a solvent carrier such as water or organic solvents, such as the alcohols (e.g. ethanol or isopropanol, acetone).

In another preferred embodiment, an inventive composition comprising a polyisoprenyl-protein inhibitor compound, a carrier and other, optional ingredients can be dispersed in an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent as well as the polyisoprenyl-protein inhibitor compound. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

Emulsifying agent carriers useful in the present invention are described hereinabove.

When the composition of the invention is an emulsion including AFC, non-lipid-based vehicles are preferred due to the lipophilic nature of the compound.

In yet, another embodiment, the inhibitors of the inventive compositions can be mixed with a gel suspension, (a semi-solid carrier) or solid carrier to form a paste, powder, ointment, cream, lotion, hydrogel or the like.

For example, ointments may be prepared which are in gel-suspension form. These are semi-solid preparations intended for external application to the epithelium. Generally, ointment bases are categorized into hydrocarbon bases (oleaginous), which may use white petroleum as a base; adsorption bases (anhydrous), which might use hydrophilic petroleum or anhydrous lanolin; emulsion bases (water and oil type); emulsion bases (oil and water type); and water soluble bases, which often use polyethylene glycol as an ointment base.

Additional compositions of the present invention using polyisoprenyl-protein inhibitor compounds and carriers can be readily prepared using technology which is known in the art such as described in *Remington's Pharmaceutical Sciences*, 18$^{th}$ or 19$^{th}$ editions, published by the Mack Publishing Company of Easton, Pa.

Preferably, the compositions of the present invention include about 0.01% to about 50% w/w of a polyisoprenyl-protein inhibitor compound. In a more preferred embodiment, the amount of the polyisoprenyl-protein inhibitor compound is about 0.1% to about 20% w/w. In an even more preferred embodiment, the amount of the polyisoprenyl-protein inhibitor compound present in the inventive composition is preferably no more than about 10% w/w. In a yet, even more preferred embodiment, the amount of the polyisoprenyl-protein inhibitor compound is less than about 5% w/w.

According to another aspect of the present invention, there is provided a method of preparing the novel compositions described hereinabove. The process generally includes admixing the at least one polyisoprenyl-protein inhibitor compound, as described hereinabove, and the pharmaceutically, cosmetically or cosmeceutically acceptable carrier. In cases where additional active ingredients, as detailed above, are present in the compositions, the process includes admixing these ingredients together with the active ingredients and the carrier. The mixing technique utilized in the process of the present invention can involve any one of the known techniques for formulating topical compositions. A variety of exemplary formulation techniques that are usable in the process of the present invention is described, for example, in Harry's Cosmeticology, Seventh Edition, Edited by J B Wilkinson and R J Moore, Longmann Scientific & Technical, 1982.

According to another aspect of the present invention, there is provided a method of treating a medical, cosmetic and/or cosmeceutical condition associated with epithelial tissues. The method is effected by topically applying, a pharmaceutically, cosmetically or cosmeceutically effective amount of the composition of the present invention as described above onto a surface.

As used herein the terms "pharmaceutically effective amount" "cosmetically effective amount" or "cosmeceutically effective amount" refer to the amount of any of the compositions of the invention that result in a therapeutic or beneficial effect following its administration to a subject. The pharmaceutical, cosmeceutical or cosmetic effect can be curing, minimizing, preventing or ameliorating a disease or disorder, improving the physical appearance and aesthetics (e.g., skin hydration), or may have any other pharmaceutical, cosmeceutical or cosmetic beneficial effect. The concentration of the substance is selected so as to exert its pharmaceutical, cosmeceutical or cosmetic effect, but low enough to avoid significant side effects within the scope and sound judgment of the skilled artisan. The effective amount of the composition may vary with the particular epithelial tissue being treated, the age and physical condition of the biological subject being treated, the severity of the condition, the duration of the treatment, the nature of concurrent therapy, the specific compound, composition or other active ingredient employed, the particular carrier utilized, and like factors.

A skilled artisan can determine a pharmaceutically effective amount of the inventive compositions by determining the unit dose. As used herein, a "unit dose" refers to the amount of inventive composition required to produce a response of 50% of maximal effect (i.e. $ED_{50}$). The unit dose can be assessed by extrapolating from dose-response curves derived from in vitro or animal model test systems.

According to this aspect of the present invention, the compositions of the present invention are preferably topically applied as needed. In another preferred embodiment, the inventive compositions are topically applied between one and four times a day, more preferably twice a day (e.g., once in the morning and once in the evening). The topical application of the compositions of the present invention is preferably carried out for a time period that ranges between 1 and 30 days, more preferably for a time period of about fourteen days. Some conditions may require topical application for an indeterminate length of time.

In one embodiment, the inventive compositions are topically administered to the epithelial surface of a subject. Non limiting examples of epithelial surfaces onto which the compositions of the present invention can be applied topically include the lateral aspect of forearms, the lateral aspect of legs, elbows, feet, backhands, back, scalp, face, buttocks, the ear canal and any other skin surfaces, and any mucosal membrane described herein. Topical application also includes applying the inventive compositions orally to the gingiva.

In another embodiment, the surface is a wound surface. In chronic wounds, topical application may include applying the inventive compositions to a non-epithelial surface such as the dermis. In yet another embodiment, the wound surface is an open wound surface. As used herein an "open wound" is a physical trauma where the skin is lacerated, cut or punctured. As used herein, "a cut" is an injury that results in a break or opening in the skin, "a laceration" is a jagged, irregular cut, and "a puncture" is a wound made by a pointed object (like a nail, knife, or sharp tooth).

Alternatively, the compositions may be administered to the epithelial condition as a component of, for example, a bandage, adhesive, or transdermal patch. In these instances, the compositions may be an integral component of the bandage, adhesive, or transdermal patch and are thereby applied to the epithelial surface.

In one preferred embodiment, the compositions of the invention are applied to the inside of a latex glove. When the skin touches the inside of the latex glove, the composition of the invention is applied to the skin. In this embodiment, the compositions of the invention act to prevent inflammation of the skin caused, at least in part, by being enclosed in the glove.

As used herein the term "treating" includes abrogating, substantially inhibiting, slowing or reversing the progression of a condition, substantially ameliorating clinical or aesthetical symptoms of a condition, substantially preventing the appearance of clinical or aesthetical symptoms of a condition, protecting from harmful or annoying stimuli or generally promoting healthy epithelial tissue.

The term "condition" includes a variety of conditions related to skin or mucosal membranes. This term is meant to include disorders or diseases, the promotion of healthy epithelium; dry skin; and inflammation caused by any underlying mechanism or disorder.

As used herein "promotion of healthy skin" or "promoting healthy skin", refers to providing cooling or soothing sensations, or reducing puffiness, or promoting the appearance of reduced wrinkling or puffiness. This phrase also refers to the subject's perception of his/her skin as appearing healthy or having the perception of wellness or youth.

In another embodiment, the inventive compositions are applied to an epithelial tissue surface to protect the surface from exposure to environmental factors. Such factors include, but are not limited to, UV radiation, wind, hot climate extremes or cold climate extremes.

In yet another embodiment, the inventive compositions are applied to prevent wrinkles. In another embodiment, the inventive compositions are applied to prevent photo-aging. In yet another embodiment, the inventive composition is administered to prevent redness or puffiness such as occurs in diaper rash.

In another embodiment, the compositions of the present invention are used to prevent dry skin. The inventive compositions can be administered to moisturize and protect the skin from the condition of dryness.

In another preferred embodiment, the compositions of the invention also are administered to treat a skin disorder that is already present, such as dry cracked skin. In another embodiment, the inventive compositions are administered to treat irritated skin, such as occurs with diaper rash.

In an even more preferred embodiment, the inventive compositions are applied to treat inflammation. As used herein "inflammation" refers to a response to infection and injury in which cells involved in detoxification and repair are mobilized to the compromised site by inflammatory mediators. Thus, the body's response may include edema, vasodilation, fever and pain. When inflammation is localized to the skin and mucosa, erythema (redness) occurs and can be treated by the compositions of this invention.

Inflammation can result from a wide variety of non-limiting conditions. These conditions include, but are not limited to, a) dermatitis, including, but not limited to, atopic dermatitis, medicamentosa, contact dermatitis, seborrheic, nummular dermatitis, chronic dermatitis of hands and feet, generalized exfoliative stasis, and localized scratches; b) acne, including, but not limited to, acne vulgaris, nodulocystic acne, acne fulminans, steroid acne, acne keloidalis nuchae, chloracne, pyoderma faciale, and cysts; c) folliculitis, including, but limited to, scalp folliculitis, spa pool folliculitis, oil folliculitis, pityrosporum folliculitis, and gram negative folliculitis; d) pseudofolliculitis barbae; e) chilblains; f) miliaria (prickly heat); g) rosacea including, but not limited to, tinea rosacea, steroid rosacea and perioral dermatitis; h) eczema and psoriasis; i) bacterial infections including, but not limited to, staphylococcal diseases, staphylococcal scalded skin syndrome, erysipelas, folliculitis, furuncles, carbuncles, paronychial infections, and erythrasma; j) surgical interventions; k) crodermatitis enteropathica; l) Sweet's disease; m) amyloidosis including, but not limited to, lichen amyloidosis and macular amyloidosis; n) hives, including, but not limited to, acute generalized and chronic generalized hives and physical hives; o) erythema annulare centrifugum and annular erythema, including, but not limited to, erythema perstans, erythema gyratum perstans, erythema gyratum repens and erythema figuratum pertans; p) bachet syndrome including, but not limited to, uveitis, erythema nodosum, biotin response, dermatoses, pyoderma gangrenosum, erythema multiforme, aphthous ulcers, granulomatous cheilitis, dermitis herpetiformis, dermatomyositis, including juvenile DM and amyopathic DM, eosinophilic fascitis; q) insect bites and animal bites and stings, including, but not limited to, sea bather's eruption, seaweed dermatitis, swimmers itch, scombroid fish poisoning, scabies, popular urticaria, and cutaneous larva migrans; r) fungal infections including, but not limited to, dermatophyte infections, tinea corporis, tinea pedis, tinea unguium, tinea capitis, tinea cruris, tinea versicolor, tinea barbae, athlete's foot, and jock itch; s) yeast infections including, but not limited to, candidiasis, such as *candida albicans*, oral candida (thrush), candidal paronychia, and; t) parasites including, but not limited to, scabies, pediculosis including pediculosis capitis, pediculosis corporis, and pediculosis pubis; and v) viral infections including, but not limited to, herpes, including simplex lesions and zoster, chicken pox (varicella) lesions, rubeola (measles) and rubella (German measles); w) vasodilation, including, but not limited to, reye's syndrome and wound healing; x) trauma from breaks in skin; y) autoimmune conditions, including, but not limited to, cutaneous lupus erythematosus; z) bullous disease, including, but not limited to, phemphigus; aa) adverse drug reactions; bb) a immune hyper-reactivity conditions including, but not limited to, polymorphic light eruption, photosensitivity, dermographism, and erythema multiforme; cc) cancer; dd) burns; ee) wounds; ff) cysts, gg) hidradinitis suppurativa hh) cellulitis.

While the compositions discussed hereinbefore do not necessarily treat the underlying disease state that may give rise to the inflamed conditions, the inventive compositions are useful for diminishing or alleviating the inflammation of the skin.

Additionally, the compositions may be used in anorectal creams and suppositories to treat conditions such as a pruritus, proctitis, anal fissures, and hemorrhoids.

The topical therapeutic compositions may further be used in ophthalmological preparations to treat inflammation such as that which results from corneal ulcers, radialkeratotomy, corneal transplants, epikeratophakia and other surgically induced wounds in the eye.

The inventive compositions also may be used orally in the form of a mouth wash or spray to protect and accelerate the healing of injured oral tissue such as mouth sores, burns or gingivitis.

The present invention described hereinabove has both human and veterinary utility. The term "subject" as used herein includes animals of, avian, reptilian or mammalian origin. Preferably, subjects are mammals. Even more preferably, subjects are human.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Dermal inflammation results in edema, erythema and tenderness. Dermal inflammation has the advantage of being rapidly induced, easily observed and rapidly measured. In addition, there are a number of factors involved in eliciting an inflammatory response. Epidermal keratinocytes, which respond directly to a irritant because of their superficial location, also, release inflammatory mediators. These mediators can act directly (1) to attract inflammatory cells to the endothelium of the dermal venules or (2) to guide inflammatory cells through the dermis to the site of inflammation after they have passed through the vascular endothelium. Alternatively, these mediators could act directly or indirectly on the vascular endothelium of the dermis to cause leakage leading to edema and/or the attraction and adhesion of circulating inflammatory cells. Thus, there are multiple G-protein and other polyisoprenyl-protein mediated signaling responses between keratinocytes and inflammatory responding cells, which may provide multiple potential targets where AFC could act to reduce inflammation. The topical delivery route has the major advantage of giving AFC nearly direct access to the site of inflammation. This avoids pharmacokinetic problems, such as drug dilution, major organ drug catabolism, and binding to serum components.

Example 1

Polyisoprenyl-Protein Inhibitor Compound AFC in an Acetone Carrier Suppresses TPA-Elicited Edema in the Murine Ear Acute Contact Irritation Model In order to assess the effects of the AFC inventive composition for reducing edema in the mouse ear model, an established model of dermal inflammation, was used. (See Carlson, R. P., et al., *Modulation of mouse ear edema by cyclooxygenase and lipoxygenase inhibitors and other pharmacologic agents*. Agents Actions, 1985. 17(2): p. 197-204; Kuehl, F. A., Jr., et al., *Role of prostaglandin endoperoxide PGG2 in inflammatory processes*. Nature, 1977. 265(5590): p. 170-3; Trancik R J, L. N., *Evaluation of topical nonsteroidal anti-inflammatory agents, in Models in Dermatology*, L. Maibach, Editor. 1985, Karger. p. 35-42; and Tramposch, K. M., *Skin Inflammation*, in *In Vivo Models of Inflammation*, M. L. Morgan D W, Editor. 1999, Birkhauser Verlag. p. 179-204.)

The standard agents for initiating inflammation are the phorbol ester, tetradecanoylphorbol acetate, (TPA) and arachidonic acid (AA). TPA produces a greater and more prolonged neutrophil infiltration response than AA (See Rao, T. S., et al., *Comparative evaluation of arachidonic acid (AA)-and tetradecanoylphorbol acetate (TPA)-induced dermal inflammation*. Inflammation, 1993. 17(6): p. 723-41.) TPA-induced inflammation is the preferred agent and was used for this example.

A. Dose Response Curve for Irritant.

A dose response range for TPA, a compound known to induce edema, was determined. TPA produces an increase in edema (ear swelling) that reaches a maximum at 6 hrs.

Increasing concentrations of TPA dissolved in acetone were applied with the aid of a micropipetter onto the right ear of each of the five 6-8 week old, male Swiss Webster mice used in this analysis. Ten microliters were spread evenly onto the inner and outer surfaces using the pipette tip. The mice were then returned to their cages. The contralateral ear was treated only with acetone. After 5.5 hours, the mice were sacrificed and 6 mm punches were taken from each ear and weighed. Edema response was expressed as a percent increase in the treated ear's weight over the untreated ear. The dose response curve, as well as an $ED_{50}$ value, was determined using the Lichtfield method (Lichtfield J T W. F., *A simplified method of evaluating dose-effect experiments*, Journal of Pharmacology and Experimental Therapeutics, 1948, 96: P. 99-113).

As seen in FIG. 1, the increase in ear weight depends on TPA dose from 0.25 to 1.75 μg/20 μl, reaching a maximum increase of approximately 150% of the acetone-treated ear. This experiment identified doses between 1.5-2.0 μg/20 μl as suitable to use in eliciting edema in future tests of anti-inflammatory agents.

B. Polyisoprenyl-Protein Inhibitor Compound AFC in an Acetone Carrier, Itself, is not an Irritant.

A range of from 5 mg to 32 mg AFC, a polyisoprenyl-protein inhibitor compound, was mixed with 20 μl acetone to produce an inventive AFC composition. Each concentration was applied with the aid of a micropipetter onto the right ear of each of six mice so that 10 μl of each of the concentrations of the AFC inventive compositions were applied to an inner ear surface and 10 μl was applied to an outer ear surface of the right ear. The AFC inventive compositions were spread evenly with a pipette tip. Each contralateral ear was treated with only acetone in the same manner. The mice then were returned to their cages. After 5.5 hours, mice were sacrificed and 6 mm punches were taken from each ear and weighed. Edema response was expressed as the percent increase in the treated ear's weight over the untreated (acetone, vehicle only) ear.

Figure 2:
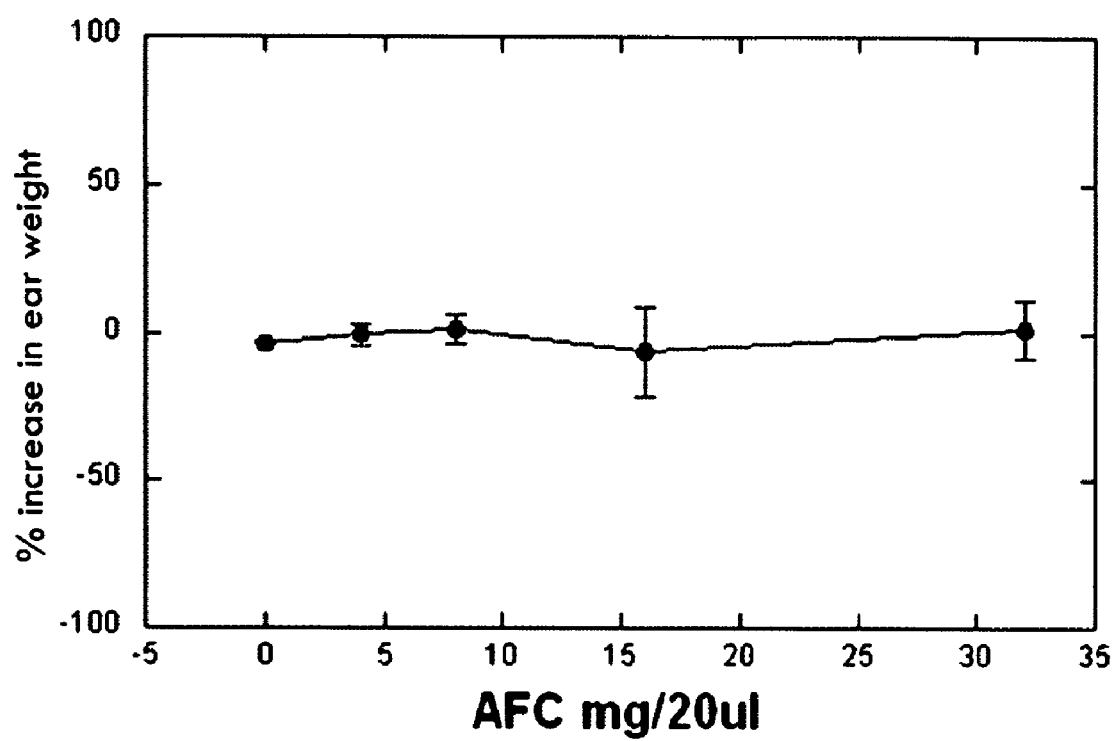

As shown in FIG. 2, AFC in acetone alone had no effect on the edema response. The AFC inventive compositions had no effect on the ear punch biopsy weight at a dose up to 32 mg/20 μl. AFC did not induce edema on its own at doses 60 fold greater than doses having efficacy against chemically-induced edema. This finding suggests an excellent safety profile for AFC.

C. Result of AFC Inventive Composition on TPA-Induced Edema.

In order to assess the effects of the inventive composition on TPA-induced edema, 2 μg of TPA in 20 μl acetone was applied with the aid of a micropipetter onto both ears of each of 6 mice. The mice were returned to their cages. Fifteen minutes later, increasing concentrations of AFC in 10 μl of acetone were applied to the inside and outside surfaces of the right ears as described above. 20 μl of an acetone vehicle was applied similarly to the left ear of each mouse as an internal negative control. After treatment, the mice were returned to their cages for 5.5 hours. The mice were sacrificed by cervical dislocation. The ears were immediately removed at their base and a 6 mm diameter punch biopsy was taken from the center of each ear. The ear punch was weighed on an analytical balance for edema measurements as described above. The ability of the various concentrations of AFC to inhibit TPA-induced edema was assessed by determining the difference in weight between the AFC-treated ear and the acetone (vehicle)-only treated ear over the increase in ear punch weight induced by TPA.

Figure 3:
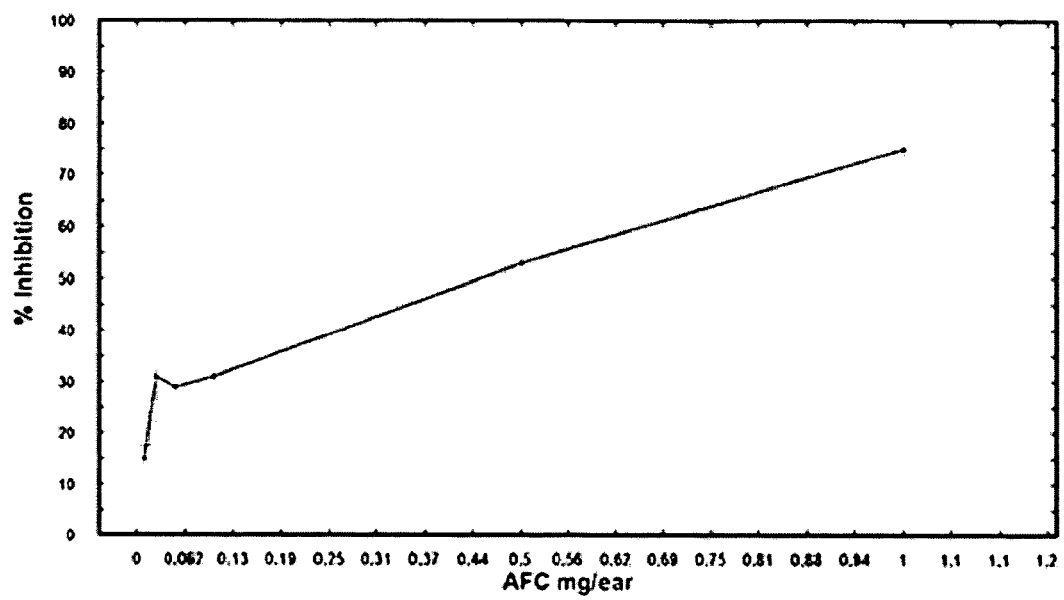
FIG. 3. AFC inhibits TPA induced edema
FIG. 4. AFC treatment produces a dose dependent inhibition of TPA induced MPO
FIG. 5. Histology of AFC inhibition of neutrophil infiltration
FIG. 6. AFC inhibits TPA-induced neutrophil infiltration
FIG. 7. AFC inhibition of TPA induced MPO activity at different application times
FIG. 8A. AFC does not effect TPA-induced MPO activity in the contralateral vehicle treated ear.

When AFC is tested in this acute inflammation mouse-ear assay, AFC reduces acute chemically induced inflammation significantly. The inventive composition reduced the TPA-induced ear weight increase in a dose dependent manner (FIG. 3). The inventive composition resulted in a maximum 80% reduction in edema. The $ED_{50}$ of the inventive AFC composition was approximately 0.44 mg/20 µl for TPA-induced edema inhibition.

Example 2

AFC Inhibits TPA-Induced Neutrophil Infiltration in Mice

A. TPA Induces Neutrophil Infiltration in Mice.

Acute contact irritants such as TPA can also induce dermal infiltration of neutrophils. This may or may not be independent of the reduction of edema, as: 1) the maximum neutrophil response is delayed relative the maximal edema response; 2) some irritants will induce edema independent of neutrophil infiltration; and 3) some of the known anti-inflammatory agents reduce one, but not the other. (See Rao, T. S., et al., *Comparative evaluation of arachidonic acid (AA)-and tetradecanoylphorbol acetate (TPA)-induced dermal inflammation*. Inflammation, 1993. 17(6): p. 723-41.) We sought to determine if topically applied AFC would affect neutrophil infiltration in response to acute topical irritation produced by TPA.

Neutrophil-infiltration Assay: Swiss Webster male mice (n=6) were treated with 1 µg/20 µl of TPA as described above in order to assess whether or not TPA induced neutrophil infiltration. Acetone was used as a control. TPA was administered as described above. The mice were returned to their cages for 24 hrs to allow neutrophil infiltration, then sacrificed by cervical dislocation. The ears were immediately removed for punch biopsy, and punches were fixed for subsequent histological analysis and MPO enzymatic assay.

MPO Assay: This assay measures myeloperoxidase, ("MPO") which is packaged in the primary granules of mature granulocytes including the neutrophil. Thus, the amount of MPO in the ear is proportional to the number of infiltrating neutrophils.

MPO enzyme activity of the ears was assayed using the technique detailed by Griffiths and coworkers (1988). To conduct the assay, each ear was homogenized in 1.0 ml of cetyltrimethylammonium bromide buffer for 5 sec using a Pro 200 tissue blender (Pro Scientific, Inc., Oxford, Conn.) at setting 5. These samples were then centrifuged for 5 minutes at 15,000 rpm in a 5415 Eppendorf microcentrifuge. Triplicate 20 microliter aliquots of supernatant were added to 200 microliters of reaction mixture (1.25 ml 1M Potassium Phosphate, 4.175 mg o-dianisidine dihydrochloride and 5 µl of 1% peroxide in a final volume of 25 ml). Absorbance at 450 nm was then measured at room temperature at three 60 second intervals using Bio-Kinetics Reader EL 312E (Bio-Tek Instruments). Activity, which was determined by a Bradford assay of the homogenate (BioRad Protein Assay, BioRad Laboratories, Inc. Hercules, Calif.) was expressed as units MPO per mg tissue +/−standard error.

Neutrophil Counting Assay: Ear punches buffered in 10% formalin in PBS at ambient temperature for a minimum of 24 hrs. were sectioned and stained with Hematoxilin & Eosin ("H&E"). The number of neutrophils, identified by their multilobular nuclei, in 6 randomly 100× magnified fields distributed along the length of the ear were manually counted. The results are expressed as the average number per field for each ear.

B. AFC Inhibits TPA-Induced Neutrophil Infiltration.

Inventive AFC compositions were used also to assess efficacy in the reduction of dermal neutrophil infiltration. (See Rao, T. S., et al., *Comparative evaluation of arachidonic acid (AA)-and tetradecanoylphorbol acetate (TPA)-induced dermal inflammation*. Inflammation, 1993. 17(6): p. 723-4 for a discussion regarding the relationship between edema and neutrophil infiltration and the effect of known anti-inflammatory agents on these variables.)

Two micrograms of TPA in 20 µl of acetone was applied onto both ears of each mouse to induce neutrophil infiltration. After 15 minutes, varying concentrations of AFC in acetone were applied to the right ear of each mouse. After 24 hours, the mice were sacrificed. The ears were removed and the efficacy of AFC on neutrophil infiltration was assessed by an MPO assay and histological analysis.

1. MPO Analysis

Figure 4:
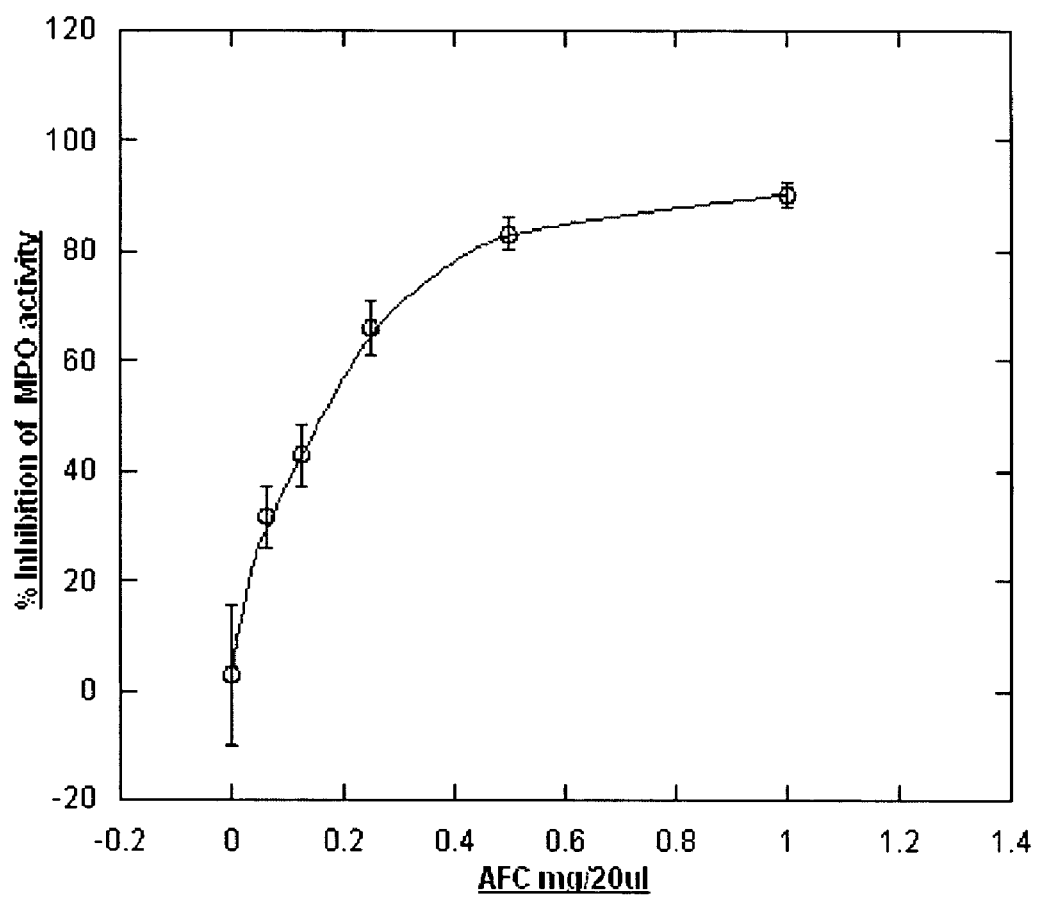

The results showed that AFC acts to reduce neutrophil infiltration in a dose dependent manner when neutrophil infiltration is measured by an MPO analysis. When AFC was tested in the Neutrophil-Infiltration Assay, it was found to have no inflammation activity of its own. The data indicate that AFC produced over an 80% inhibition of TPA-induced increases in MPO activity and had an $ED_{50}$ of 0.065 mg/20 µl (FIG. 4).

Figure 5:
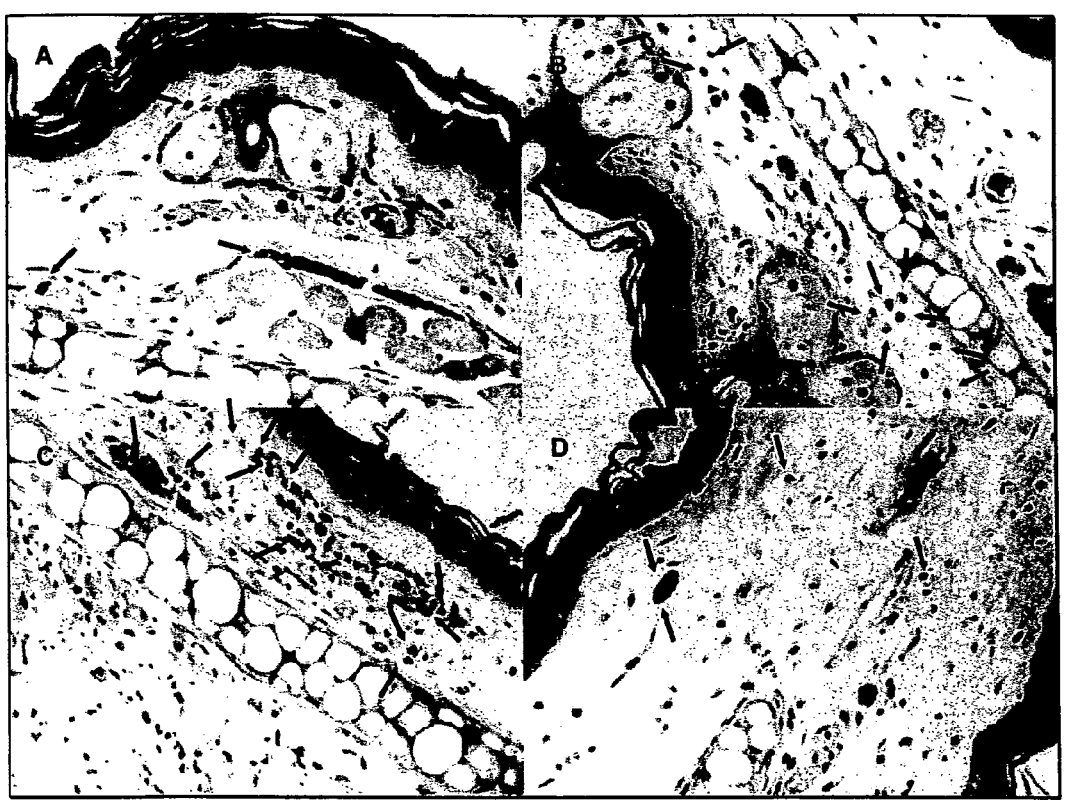

2. Neutrophil Counts:

This histological analysis demonstrated the efficacy of AFC in suppressing dermal neutrophil infiltration in response to acute contact irritation. As seen in FIG. 5, the presence of neutrophils in the TPA alone treated ears was clearly observed 24 hours after treatment. Essentially no neutrophils were observed in the ears that were not exposed to TPA. In the ears pretreated with TPA and then treated with vehicle or AFC, the numbers of neutrophils were comparable between vehicle plus TPA-treated ear and ears treated with TPA alone. A substantial reduction of neutrophils can be observed in the AFC treated ear.

Figure 6:
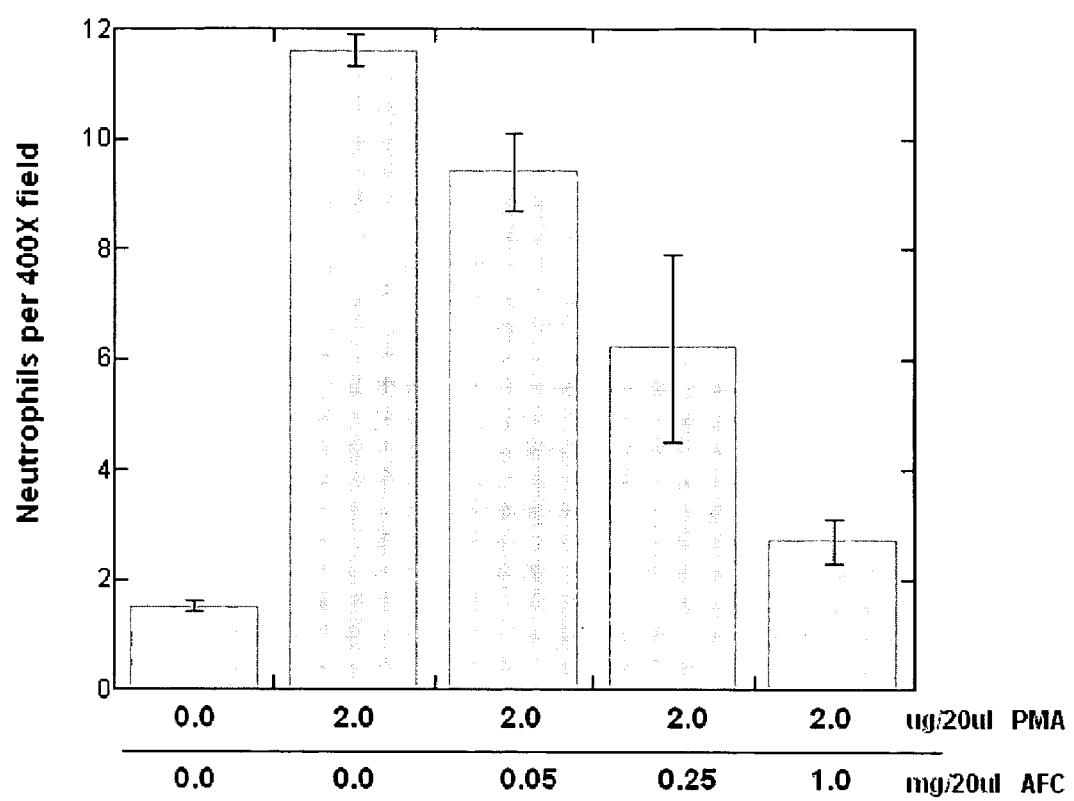

Upon counting the neutrophils, (FIG. 6) 1.0 mg/20 µl of AFC produced a statistically significant 80% reduction in dermal neutrophils produced in response to acute contact irritation by TPA. (Statistical significance was calculated using a Student's paired t-test).

C. The Effect of AFC on Neutrophils is Time Dependent

The effectiveness of AFC treatment at various times before and after TPA application was assessed using MPO as a measure of neutrophil infiltration. In this example, both ears of six mice were treated with a 1 µg/20 µl dose of TPA in acetone. The right ear was then treated with 1 mg/20 µl AFC inventive composition at various times before and after TPA application, while simultaneously treating the contralateral ear with acetone.

Figure 7:
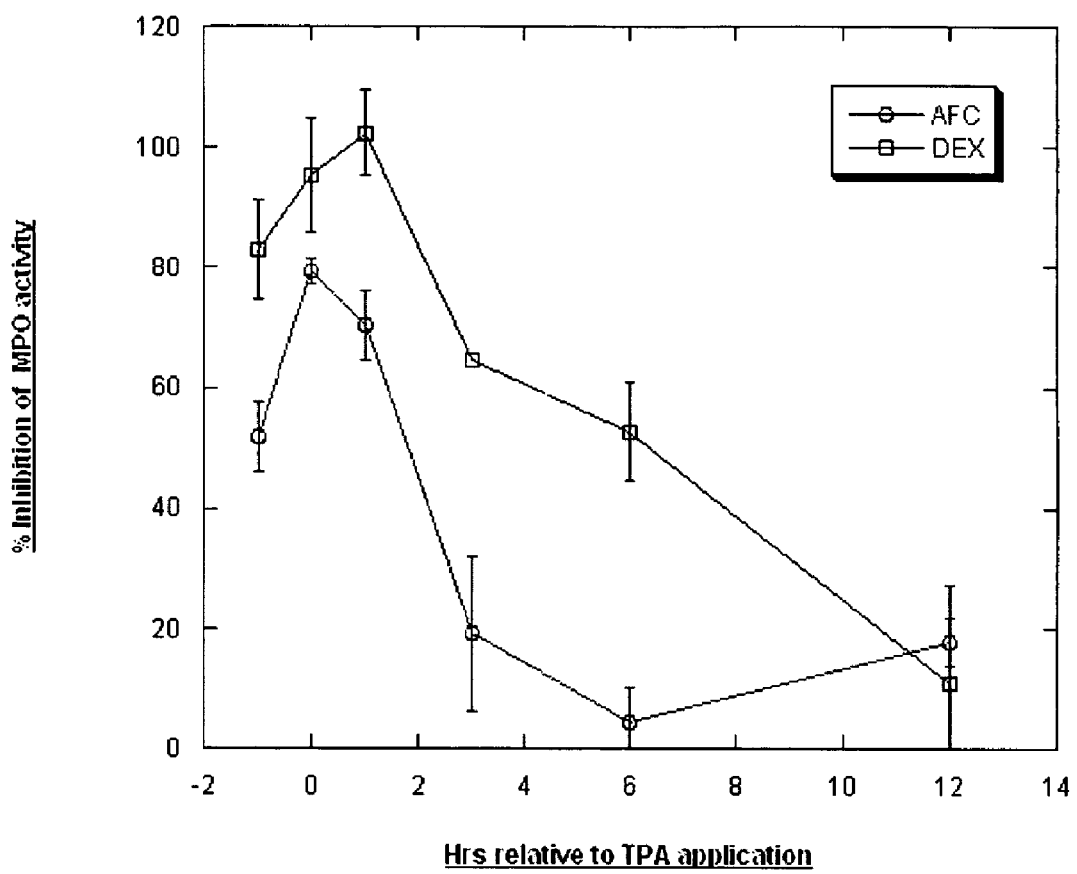

The results show the efficacy of AFC treatment prior to, simultaneous with, or after exposure of skin to TPA (FIG. 7). There was a gradual decrease in MPO activity with time at which AFC was applied after TPA application, the steroid dexamethasone showed a similar time dependence. Thus, it can be anticipated that AFC will act like steroids in reducing established inflammatory conditions.

These results support a wide range of possible cosmetic and pharmaceutical applications for AFC.

Example 3

The AFC Inventive Composition does not Exhibit Systemic Effects

The effect of AFC on TPA induction of neutrophil MPO activity was compared with two other agents representing different classes of commonly used anti-inflammatories that inhibit inflammation by mechanisms different from AFC. These included dexamethasone, a steroid, and indomethasone, a non-steroid anti-inflammatory drug, which targets cycloxygenases. The action of AFC in this model was, therefore, compared to that of dexamethasone and indomethasone. Each of these agents were tested using the same protocols used to test AFC.

Figure 8A:
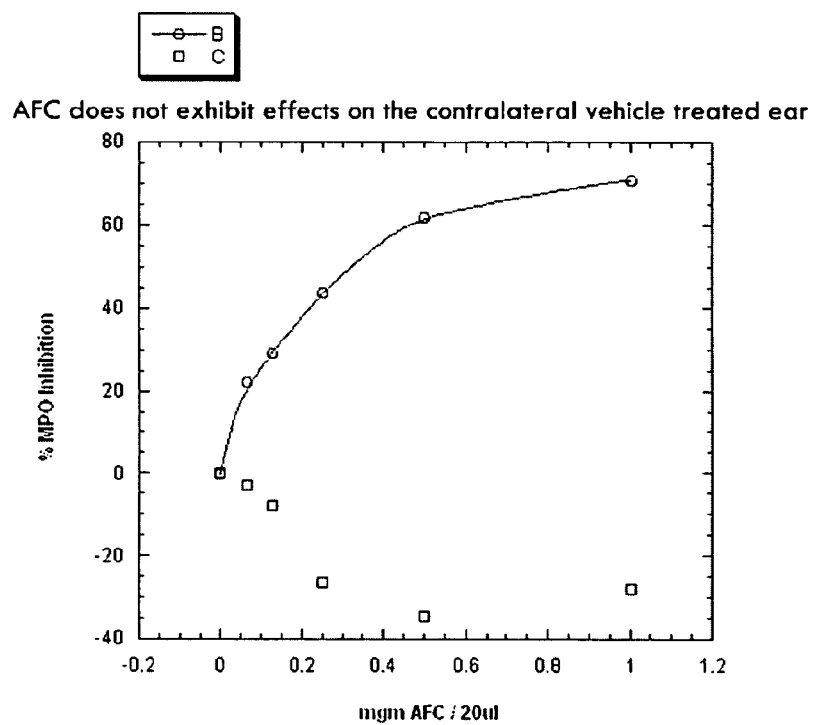
FIG. 8B. Dexamethasone acts to increase inhibition of TPA-induced MPO activity in the contralateral vehicle treated ear
FIG. 8C. Indomethacin acts to increase inhibition of TPA-induced MPO activity in the contralateral vehicle treated ear.
Figure 8B:
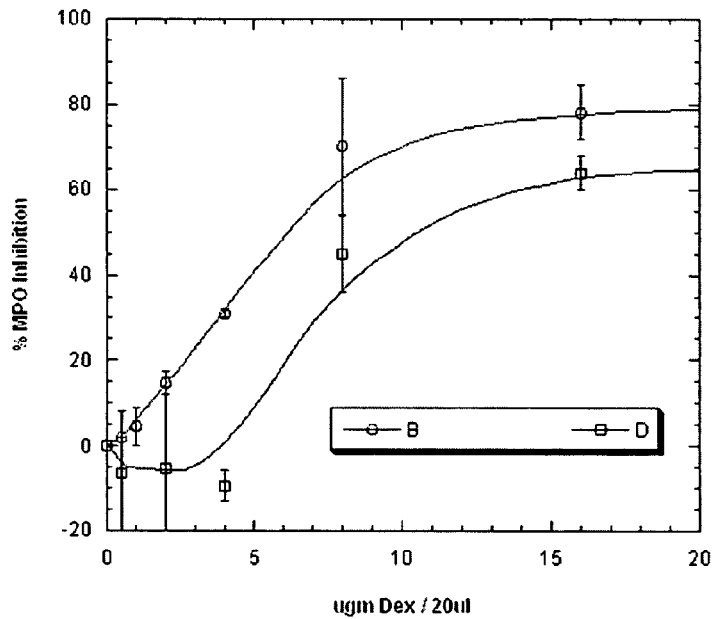
Figure 8C:
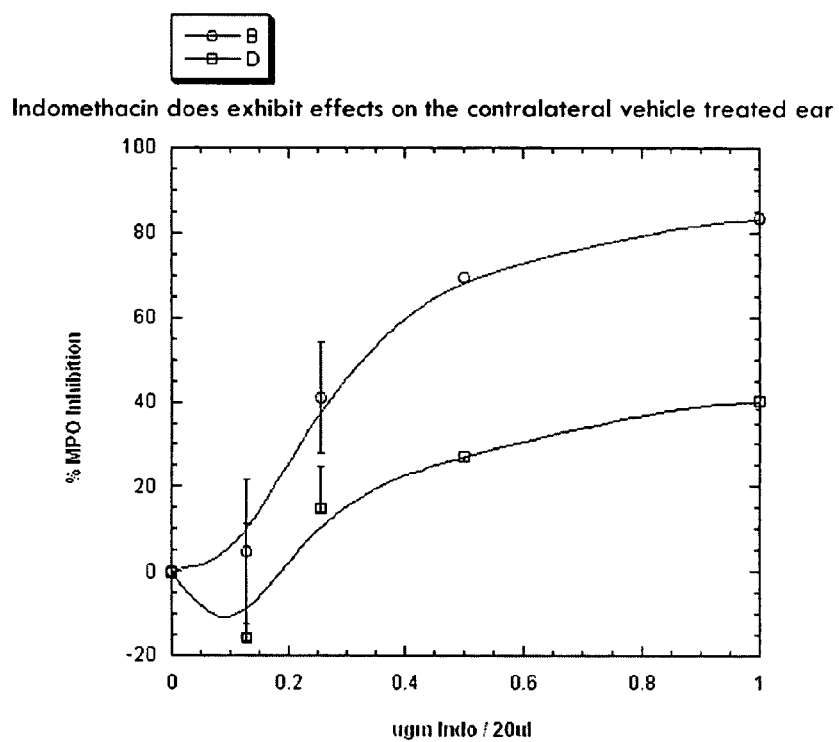

As shown in FIGS. 8B and 8C, when the concentration of dexamethasone and indomethasone is increased, the contralateral vehicle-treated ear shows increasing inhibition of MPO activity, reflective of inhibition of neutrophil infiltration. This is evidence that topically applied dexamethasone and indomethasone are entering the circulation and exerting a systemic effect with increasing effective local doses. With AFC, no effect was seen on the vehicle-treated ear (FIG. 8A). Topically applied AFC, even at its highest effective local doses is not entering the circulation and, therefore, has no systemic effect in the mouse model.

Example 4

Effect of an AFC and Acetone Composition on Arachadonic Acid-Induced Edema and Arachadonic Acid-Induced Neutrophil Infiltration Aracadonic acid ("AA"), another standard agent that is routinely used as a contact irritant in the mouse ear model to assay the effectiveness of both steroidal and nonsteroidal anti-inflammatory agents, is the metabolic precursor for a number of lipoxygenase and cyclooxygenase products. Its mechanism of action and, thus, the signaling pathways it activates, differ from those activated by topically applied TPA. AA produces a more rapid edema than TPA that peaks at 1 hr after application. There is minimal histologically observable neutrophil infiltration in response to AA, but an increase in MPO can be detected. Experience has shown that effectiveness against cyclooxygenase activated inflammation in this model is less predictive of effectiveness against human inflammatory diseases than effectiveness against TPA activated inflammation.

The effect of the inventive compositions on arachidonic acid (AA)-induced inflammation was assayed using the same protocols as above, but with the following modifications. AA was applied to both ears at 4 mg/40 µl acetone. The ears were harvested at 1 hr to measure edema, the maximum response time, and at 5 hr for inflammatory neutrophil infiltration as measured by an MPO assay.

Figure 9:
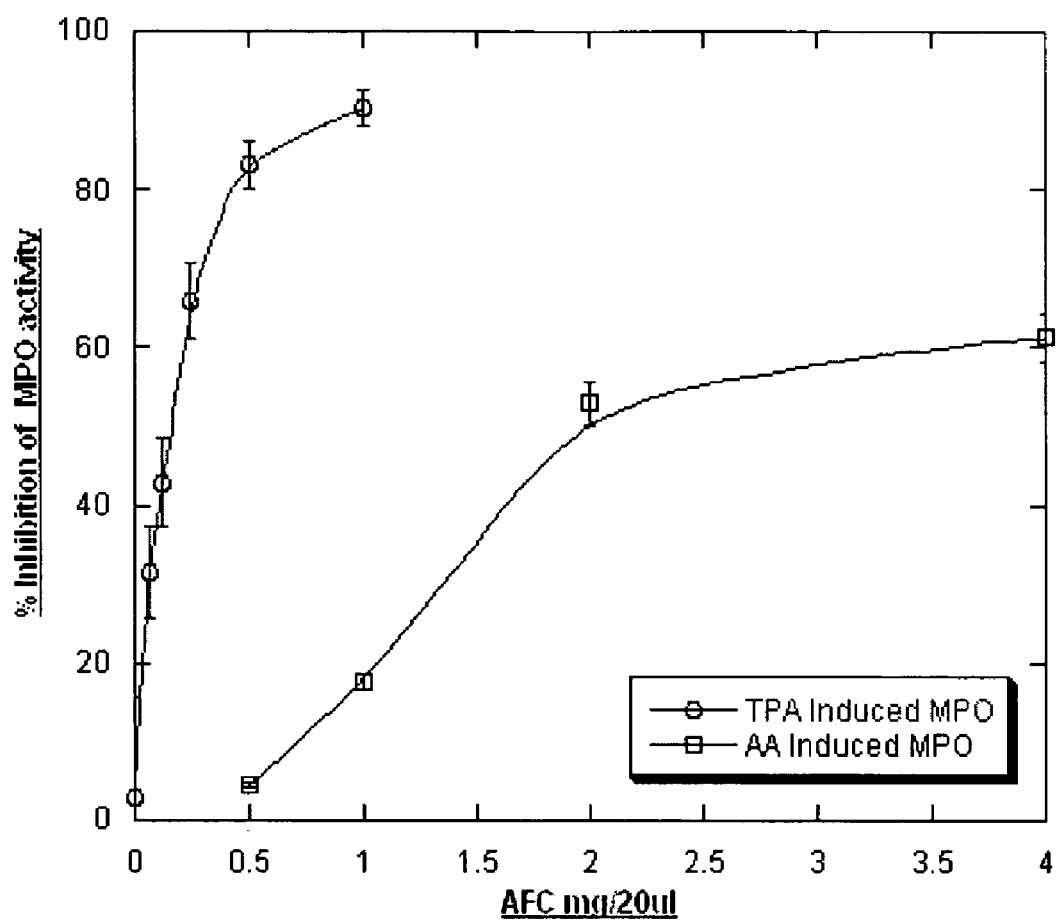
FIG. 9. AFC inhibits AA induced induced MPO.

The AFC inventive composition, prepared as described above, is less effective in reducing granulocyte infiltration induced by AA than TPA. It has 50% of the activity of TPA and a 10 fold higher $ED_{50}$ (FIG. 9).

Example 5

AFC Inventive Composition Visibly Reduces TPA-Induced Erythema

Figure 10:
FIG. 10. AFC reduces TPA-induced erythema
FIG. 11. Inhibition of contact dermatitis in a volunteer

For this example, both ears of a mouse were treated with a 1 µg/20 µl dose of TPA in acetone. After 1 hour, the right ear was treated with 1 mg/20 µl of inventive AFC composition and the left ear was treated with acetone alone. The photo was taken 23 hours later using a Nikon D70 digital camera. We have observed an effect of the AFC inventive composition on TPA-induced erythema (FIG. 10).

Example 6

AFC Inventive Compositions Reduce Inflammation in Humans when Pre-Applied

Figure 11:
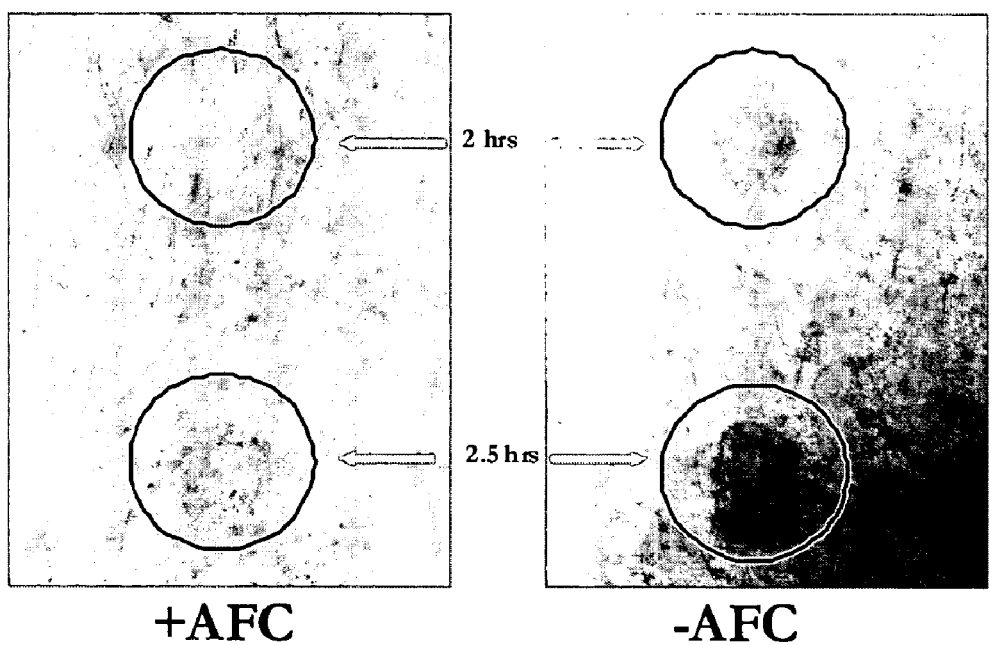

An irritant was applied to the middle of the upper back of a human subject using a 0.2 ml 20% SDS solution and a Hill-Top Chamber patch with Webril pad. AFC, at a concentration of 140 mM in aqueous formulation, was pre-applied to patch areas 1a and 1b (FIG. 11). Patches 1a and 2a were removed after 2 hours, while patches 1b and 2b were removed after 2 hours and 30 minutes. High levels of irritation were visible in patch sites 2a and 2b. Site 1a showed normal skin while 1b showed a mild response. These results show that the inventive composition can reduce or prevent inflammation when human skin is exposed to an irritant.

Example 7

The Effect of AFC on Chronic Irritation in Mice

The effectiveness of the inventive compositions against established chronic irritation is assayed using a modification of the technique of Stanley P L et al., *Mouse skin inflammation induced by multiple topical application 12-O-tetradeconoyphorbol-13-acetate. Skin Pharmacol.* 1991, 4: p 262-271. (1991). Both ears of each mouse are treated with TPA in acetone, as above, in a series of 5 applications on the mornings of days 0, 2, 4, 7, and 9. The treated ear receives the inventive compositions containing AFC and acetone, in series of three paired applications, such that it is applied 6 hr apart on days 7, 8 and 9. Punches of the ears are taken the afternoon of the tenth day and prepared, as above, for the edema assay and the infiltration of neutrophils. Total granulocyte infiltration is assayed by measuring MPO activity. Macrophage infiltration is determined immunocytologically using the MOMA-2 antibody. Hydrocortisone, which is known to reduce inflammatory edema granulation infiltration and microphage infiltration, is used as a positive control. The results will show that AFC in acetone reduces chronic edema and neutrophil number in mice.

Example 8

The Effect of the AFC Inventive Composition on Delayed-Type Hypersensitivity

The mouse ear model, described above, is modified to assay the effect of anti-inflammatory agents in an immune based inflammation model (See Tramposch, K. M., *Skin Inflammation,* in *In Vivo Models of Inflammation,* M. L. Morgan D W, Editor. 1999, Birkhauser Verlag. p. 179-20 and Chapman, J. R., Z. Ruben, and G. M. Butchko, *Histology of and quantitative assays for oxazolone-induced allergic con-*

*tact dermatitis in mice.* Am J Dermatopathol, 1986. 8(2): p. 130-8). In this model, a sensitizing dose of dinitrofluorobenzene ("DNFB") 1-3% in acetone is applied topically according to a modification of the method by Back et al. (See Back, O. and T. Egelrud, *Topical glucocorticoids and suppression of contact sensitivity. A mouse bioassay of anti-inflammatory effects.* Br J Dermatol, 1985. 112(5): p. 539-45 and Bailey, S. C., et al., *A novel contact hypersensitivity model for rank-ordering formulated corticosteroids.* Inflamm Res, 1995. 44 Suppl 2: p. S162-3) to the shaved bellies of mice to elicit an immune response. Mice are challenged on day 5 with 40 µl of 0.5-1% DNFB to each ear. The AFC inventive compound is applied either 0.5 hr before or 15 min after the challenge to one ear and the vehicle is applied to the other ear. The ears are assayed for edema or neutrophil infiltration 5 hr later. Dexamethasone is used as a positive control. Five days later, the ears are challenged topically with a dose of DNFB insufficient to produce contact irritation. Simultaneously, cell infiltration studies are initiated. Initially, there are more neutrophils than macrophages. By 48-72 hrs, macrophages become the predominant population. No inflammatory response is seen. The inventive AFC composition is, therefore, effective in reducing both edema and neutrophil infiltration.

We claim:

1. A method comprising:
   applying onto a skin surface of a mammal suffering from or susceptible to epidermal irritation, epidermal redness, or epidermal inflammation, a topical composition comprising:
   about 0.1% to about 5% w/w N-acetyl-S-farnesylcysteine ("AFC"), also referred to as N-acetyl-S-trans, trans-farnesyl-L-cysteine, or a pharmaceutically acceptable salt thereof, and
   a carrier selected from the group consisting of water, ethanol, isopropanol, acetone, and combinations thereof,
   wherein the composition inhibits the epidermal irritation, epidermal redness, or epidermal inflammation locally on the skin surface of the mammal, without systemic anti-inflammatory effects.

2. The method of claim 1 wherein the mammal is a human.

3. The method according to claim 1, wherein the carrier comprises at least one agent selected from the group consisting of a moisturizing agent, a pH adjusting agent, a deodorant agent, a fragrance, a hair-conditioning agent, a chelating agent, a preservative, an emulsifier, a thickener, a solubilizing agent, a penetration enhancer, an anti-irritant, a colorant, a surfactant, and combinations thereof.

4. The method according to claim 3, wherein the moisturizing agent is selected from the group consisting of guanidine, glycolic acid, glycolate salts, aloe vera, allantoin, urazole, polyhydroxy alcohols, propylene glycol, butylene glycol, hexylene glycol, polyethylene glycols, sugars, starchs, alkoxylated glucose, hyaluronic acid, lactamide monoethanolamine, acetamide monoethanolamine, and combinations thereof.

5. The method according to claim 1, wherein the composition is formulated as a mouthwash, a rinse, or an oral spray.

6. The method according to claim 5, wherein the composition has a pH from about 5 to about 6.5.

7. The method according to claim 5, wherein the composition further comprises at least one agent selected from the group consisting of a fluorine-providing compound, a sweetening agent, a coloring agent, a moisturizer, an emulsifier, and combinations thereof.

8. The method according to claim 1, wherein the carrier is a pharmaceutically acceptable carrier.

9. The method according to claim 8, wherein the composition is formulated so that the AFC is delivered with delayed release.

10. The method according to claim 9, wherein the carrier is selected from the group consisting of a liposome, a microsponge, a microsphere and a microcapsule.

11. The method according to claim 1, wherein the carrier is a cosmetically acceptable carrier.

12. The method according to claim 1, further comprising a second active ingredient.

13. The method according to claim 12, wherein the second active ingredient comprises at least one ingredient selected from the group consisting of a protective agent, an emollient, an astringent, an irritant, a keratolytic agent, a sun screening agent, a sun tanning agent, an antibiotic agent, an antifungal agent, an antiviral agent, an antiprotozoal agent, an anti-acne agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, a hormone, an anti-dandruff agent, an anti-wrinkle agent, an anti-skin atrophy agent, a sclerosing agent, a cleansing agent, a caustic agent, a hypopigmenting agent, and combinations thereof.

14. The method according to claim 13, wherein the protective agent is selected from the group consisting of an adsorbent, a demulcent, a dessicant, and combinations thereof.

15. The method according to claim 13, wherein the irritant is a rubefacient.

16. The method according to claim 1, wherein the step of applying comprises applying the composition to skin at a site selected from the group consisting of nose, mouth, ear, eye, vagina, rectum, and combinations thereof.

17. The method according to claim 1, wherein the epidermal irritation, epidermal redness, or epidermal inflammation is associated with a condition selected from the group consisting of dermatitis, acne, folliculitis, pseudofolliculitis barbae, chilblains, miliaria, rosacea, eczema, psoriasis, bacterial infections, surgical interventions, crodermatitis enteropathica, Sweet's disease, hives, erythema annulare centrifugum, bachet syndrome, an insect bite, an animal bite, a sting, a fungal infection, a yeast infection, a parasite, a viral infection, a vasodilation, a trauma, a bullous disease, an adverse drug reaction, a immune hyper-reactivity condition, a cancer, a burn, a wound, a cyst, hidradinitis suppurativa, and cellulitus.

18. The method according to claim 1, wherein the composition is in the form of an emulsion.

19. The method according to claim 1, wherein the composition is in the form of a gel suspension.

20. The method according to claim 19, wherein the gel suspension is incorporated into a composition selected from the group consisting of an ointment, an oil, a bandage, a lotion, a paste, a powder, a gel and a cream.

21. The method according to claim 1, wherein the composition further comprises a retinoid.

22. The method according to claim 21, wherein said retinoid is at least one of vitamin A, retinol, retinal, retinyl palmitate, retinoic acid, tretinoin or iso-tretinoin or a mixture thereof.

23. The method according to claim 1, wherein the composition further comprises an alpha-hydroxy acid.

24. The method according to claim 23, wherein said alpha-hydroxy acid is at least one of glycolic acid, lactic acid, tartaric acid, malic acid or citric acid or a mixture thereof.

25. The method according to claim 1, wherein the composition further comprises a beta-hydroxy acid.

26. The method according to claim 1, wherein the composition further comprises titanium oxide, zinc oxide, benzoyl peroxide, fluorouracil, resorcinol, or salicylic acid or a mixture thereof.

27. The method according to claim 1, wherein the composition further comprises hyaluronic acid.

28. The method according to claim 1, wherein the composition further comprises glycerin.

29. The method according to claim 1, wherein the composition has a pH between 4.0 and 7.0.

30. A method comprising:
applying onto a skin surface of a mammal suffering from or susceptible to epidermal irritation, epidermal redness, epidermal inflammation:
an amount of a topical composition comprising about 0.1% to about 5% w/w N-acetyl-S-farnesylcysteine ("AFC"), also referred to as N-acetyl-S-trans, trans-farnesyl-L-cysteine, and
a carrier selected from the group consisting of water, ethanol, isopropanol, acetone, and combinations thereof, wherein said topical composition promotes healthy skin, without systemic effect.

31. The method of claim 30, wherein the mammal is a human.

32. The method according to claim 30, wherein the skin surface is an epithelial surface.

33. The method according to claim 32, wherein the epithelial surface is selected from a group consisting of a lateral aspect of forearm, a lateral aspect of a leg, elbow, feet, backhands, scalp, face, buttocks, ear canal and eye.

34. The method according to claim 30, wherein the step of applying comprises applying the composition on a wound surface.

35. The method according to claim 30, wherein the step of applying comprises applying to a site characterized by puffiness.

36. The method according, to claim 30, wherein the step of plying comprises applying to a site characterized by wrinkling.

37. The method according to claim 30, wherein the step of applying comprises applying the composition to a site characterized by photoaging.

38. The method according to claim 30, wherein the step of applying comprises applying the composition on irritated skin surface.

39. The method according to claim 30, wherein the step of applying comprises applying to a site including dry skin.

40. The method according to claim 30, wherein the step of applying comprises applying the composition to a site characterized by redness of skin.

41. The method according to claim 30, wherein the composition has a pH from about 4.0 to about 7.0.

42. The method according to claim 1 or claim 30, wherein the composition has a pH from about 5.0 to about 6.0.

* * * * *